(12) United States Patent
Lu et al.

(10) Patent No.: US 8,790,925 B2
(45) Date of Patent: Jul. 29, 2014

(54) METHODS OF GENERATING HYPER INOS EXPRESSING CELLS AND USES THEREOF

(71) Applicant: Case Western Reserve University, Cleveland, OH (US)

(72) Inventors: Kurt Q. Lu, Cleveland Heights, OH (US); Kevin D. Cooper, Moreland Hills, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 13/780,503

(22) Filed: Feb. 28, 2013

(65) Prior Publication Data

US 2014/0170165 A1 Jun. 19, 2014

Related U.S. Application Data

(63) Continuation of application No. 13/578,785, filed as application No. PCT/US2011/024757 on Feb. 14, 2011, now abandoned.

(60) Provisional application No. 61/303,871, filed on Feb. 12, 2010, provisional application No. 61/434,151, filed on Jan. 19, 2011, provisional application No. 61/320,879, filed on Apr. 5, 2010.

(51) Int. Cl.
*C12N 5/0786* (2010.01)
*A61K 31/425* (2006.01)
*A61K 31/21* (2006.01)

(52) U.S. Cl.
USPC .......................... 435/375; 514/369; 514/510

(58) Field of Classification Search
None
See application file for complete search history.

(56) References Cited

U.S. PATENT DOCUMENTS

2006/0078533 A1* 4/2006 Omoigui .................. 424/78.14

* cited by examiner

*Primary Examiner* — Daniel C Gamett
(74) *Attorney, Agent, or Firm* — Tarolli, Sundheim, Covell & Tummino LLP

(57) ABSTRACT

A method of generating a hyper iNOS expressing cell includes administering to a myeloid derived cell an amount of a PPARγ agonist and an IL-6/STAT3 signaling pathway antagonist effective to substantially inhibit STAT3 activation in the cell and administering an inflammatory insult to the cell to stimulate hyper iNOS expression from the cell.

19 Claims, 23 Drawing Sheets

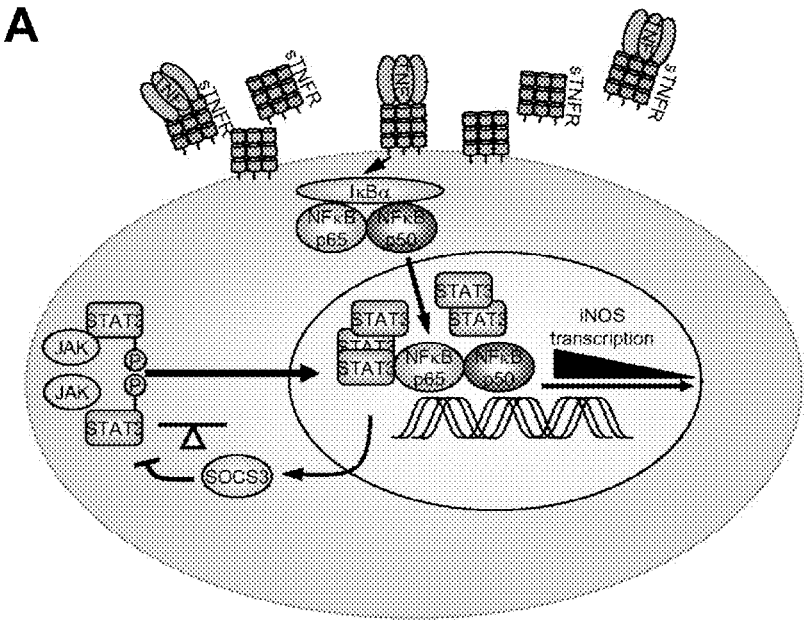
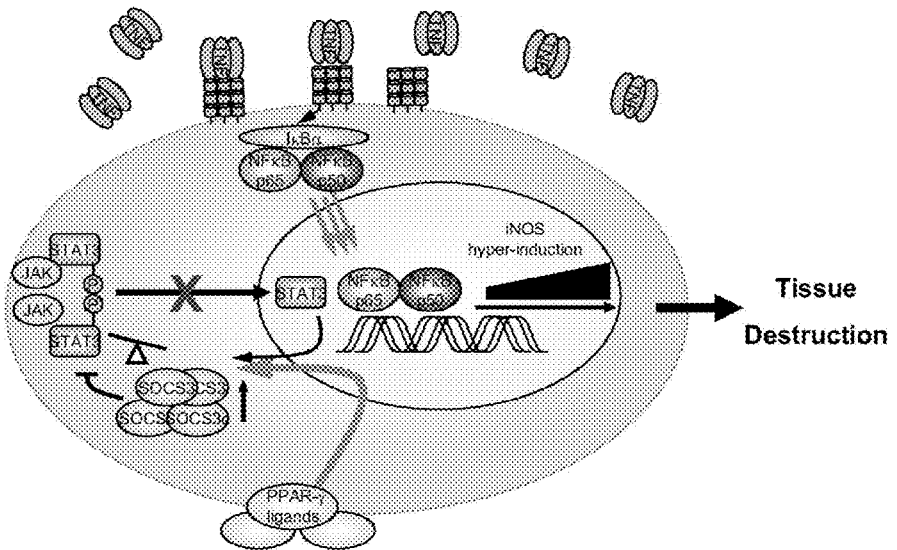
Figs. 1A-B

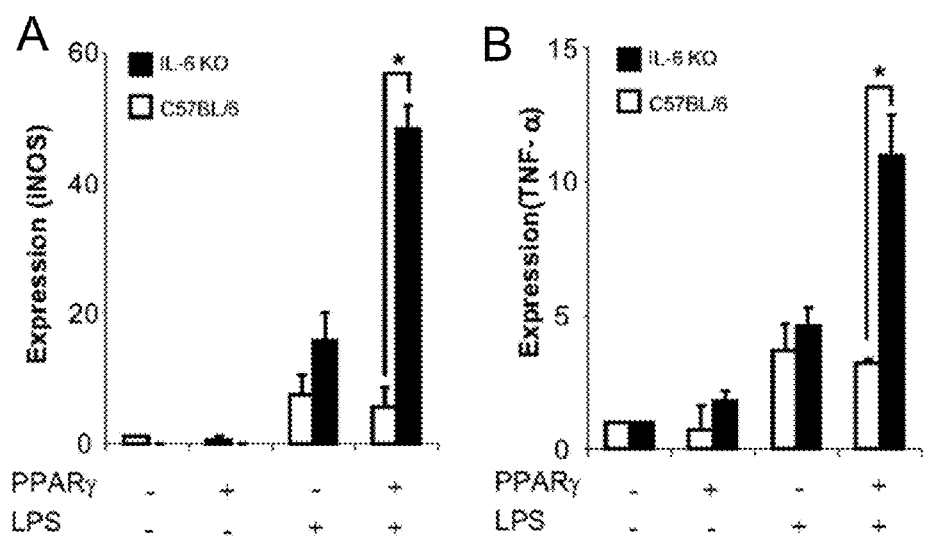
Figs. 2A-B
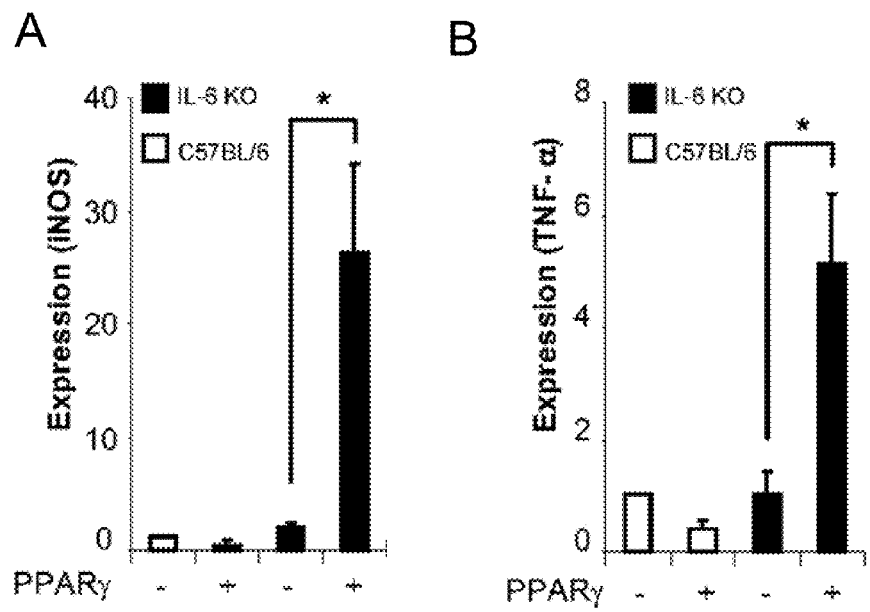
Figs. 3A-B

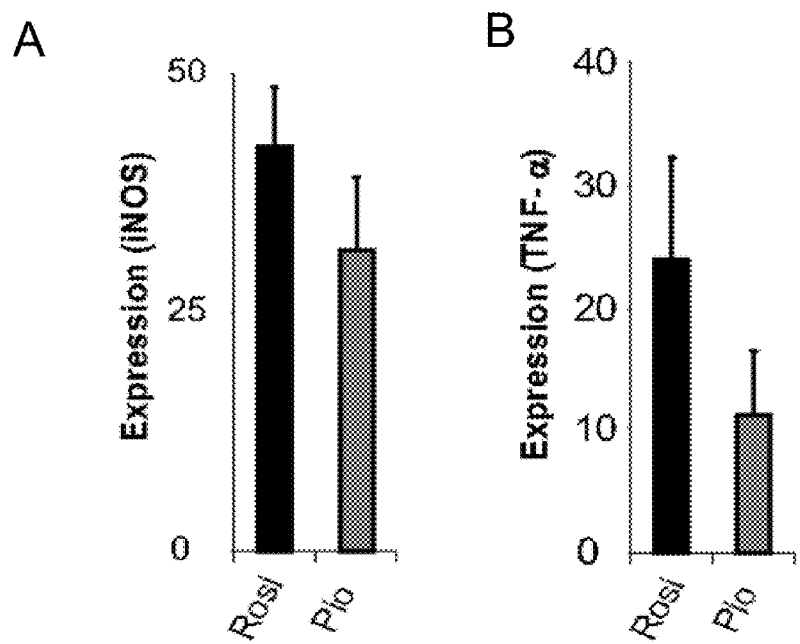
Figs. 4A-B
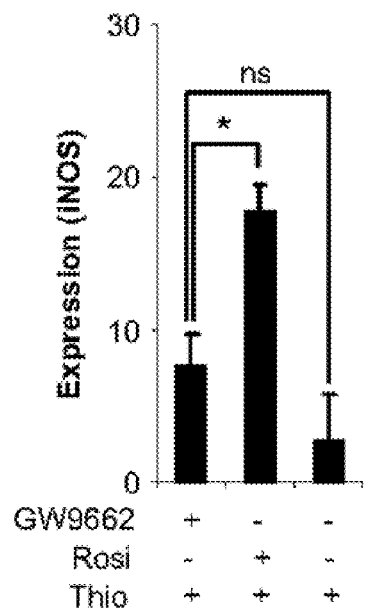
Fig. 5

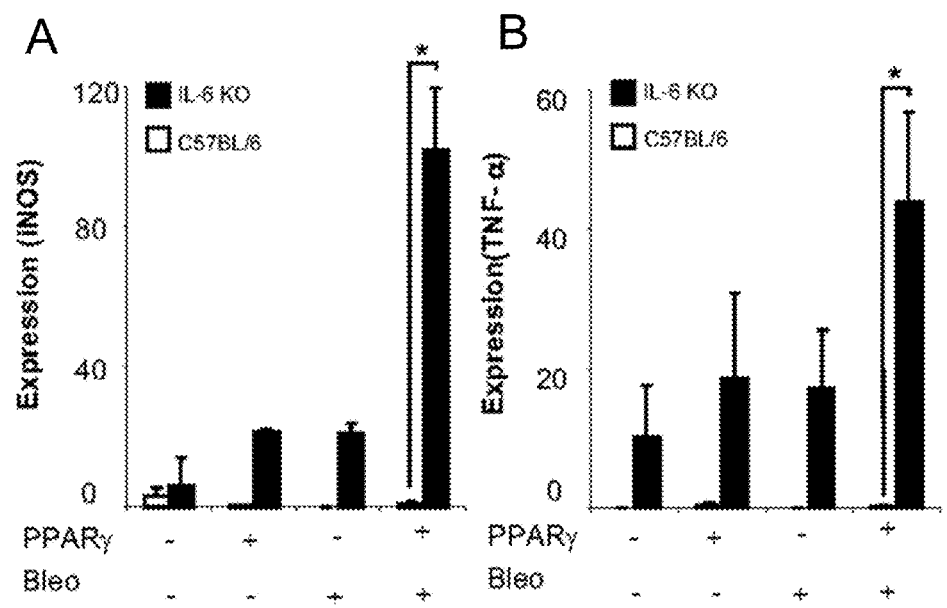
Figs. 6A-B
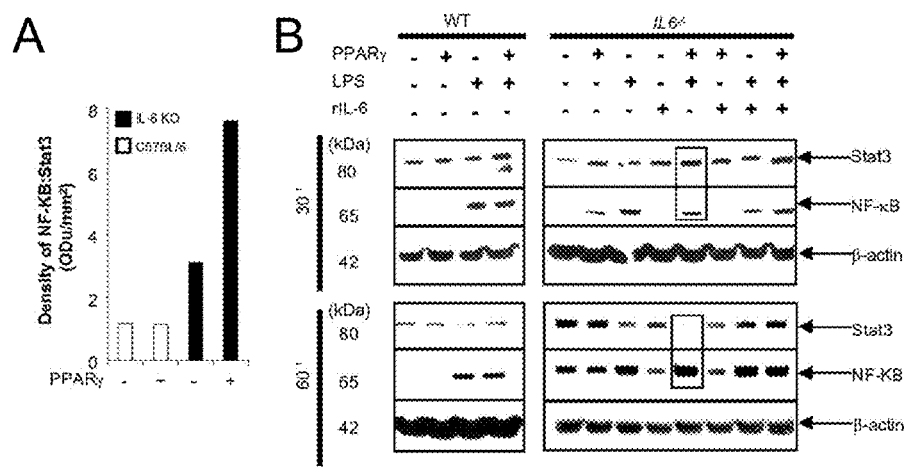
Figs. 7A-B

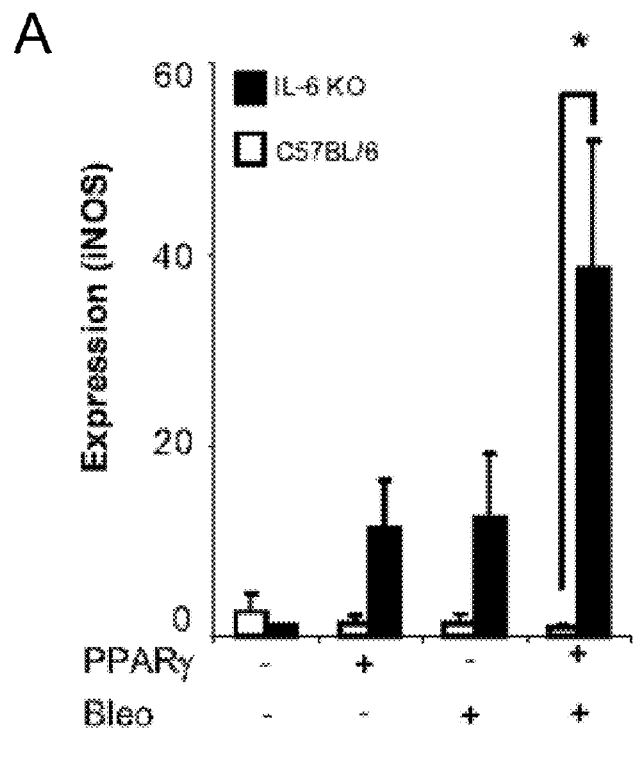
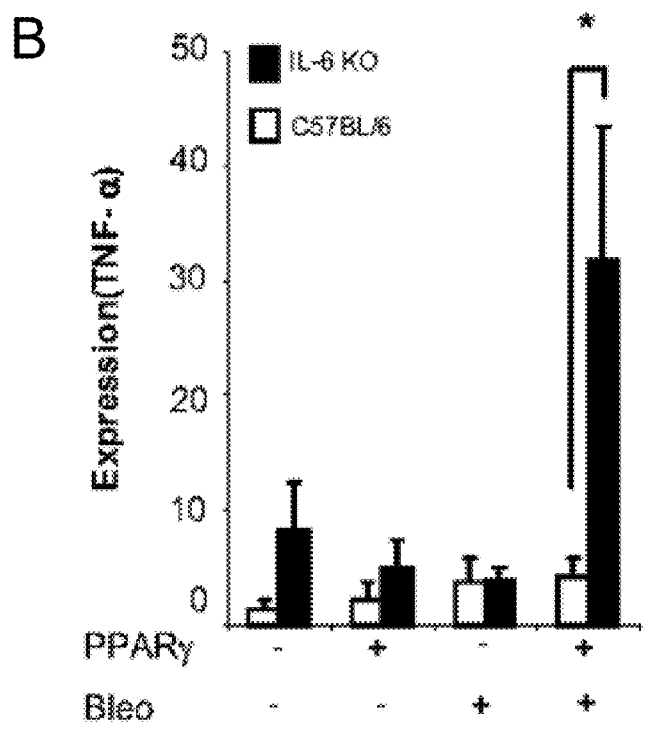
Figs. 8A-B

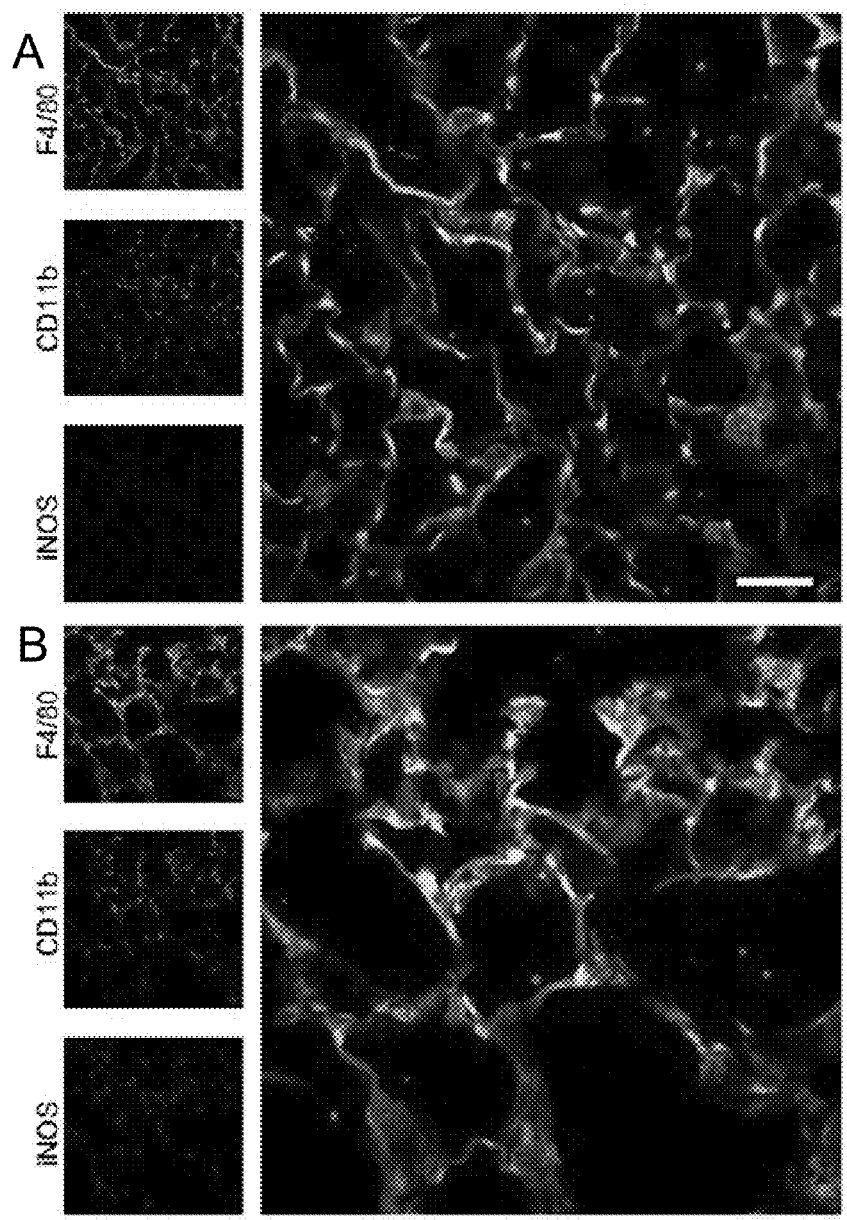
Fig. 9A-B

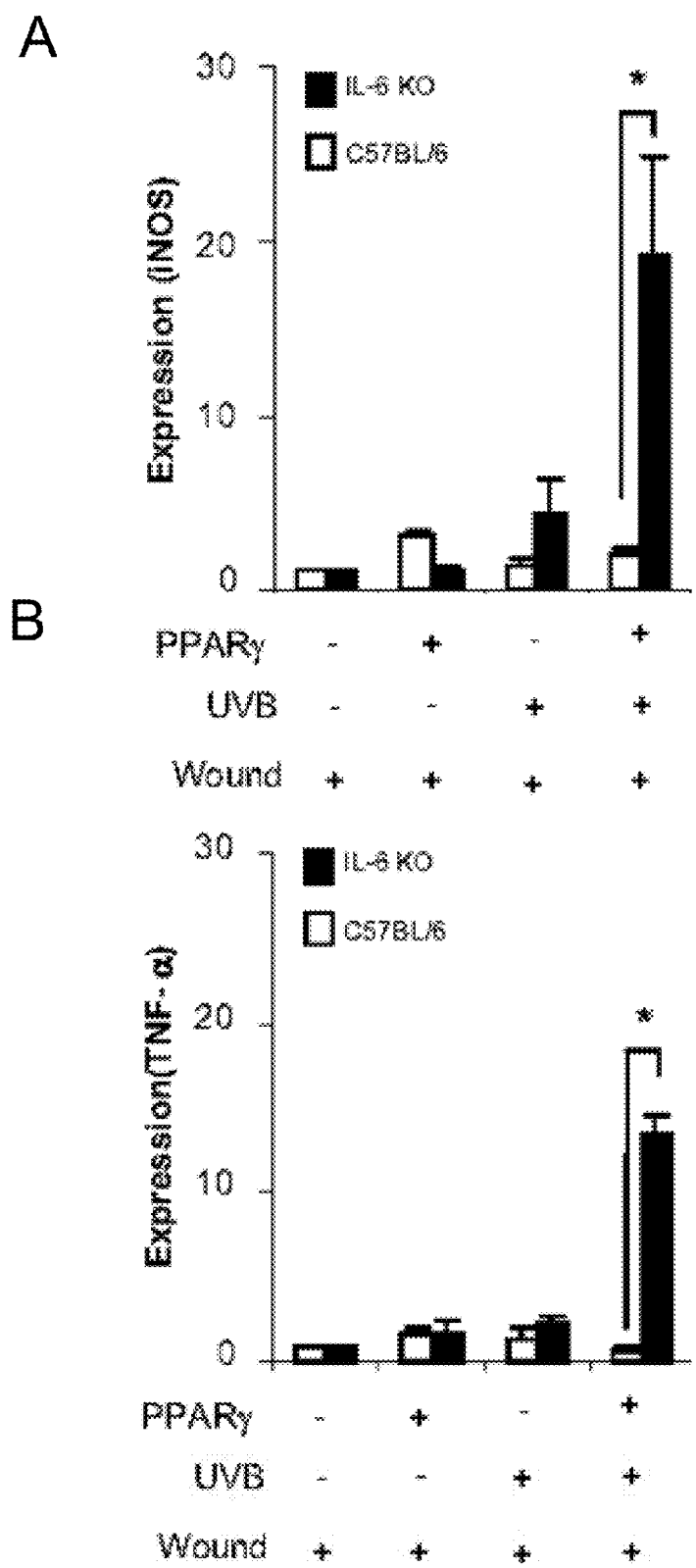
Figs. 10A-B

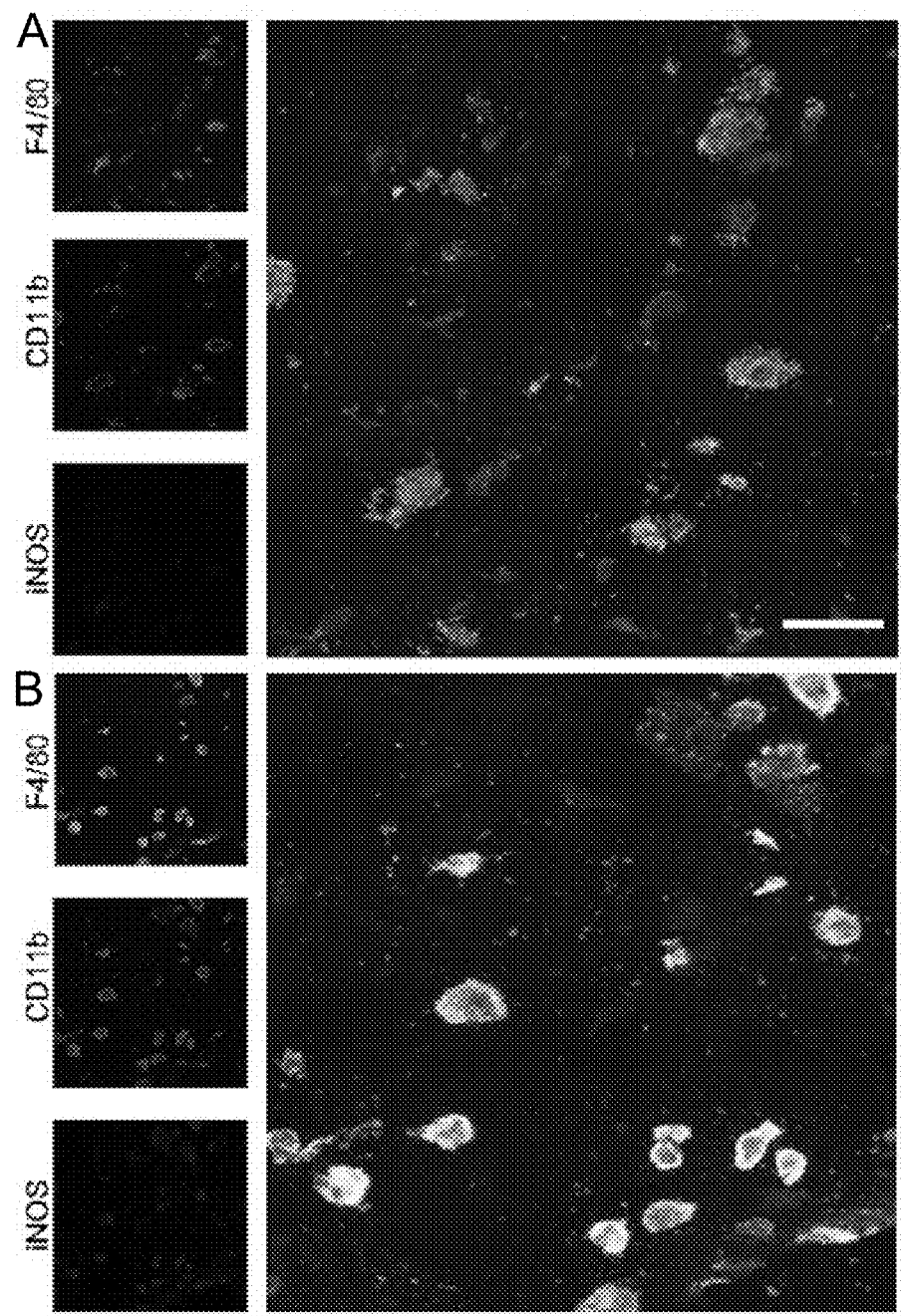
Figs. 11A-B

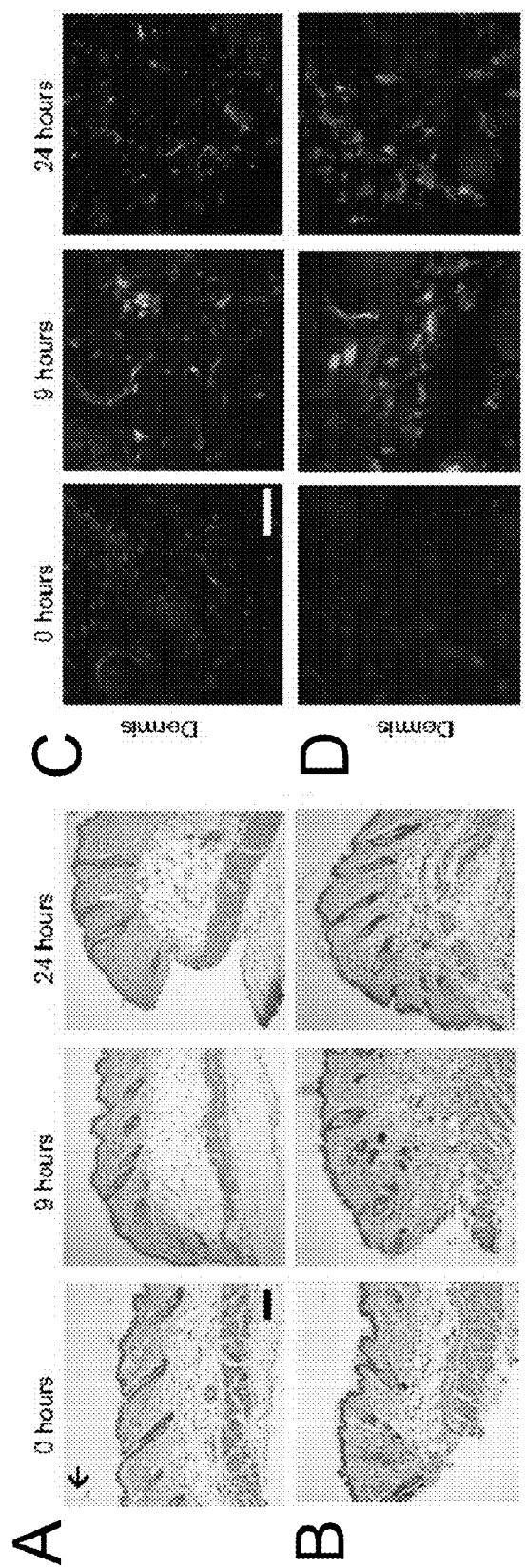
Figs. 12A-D

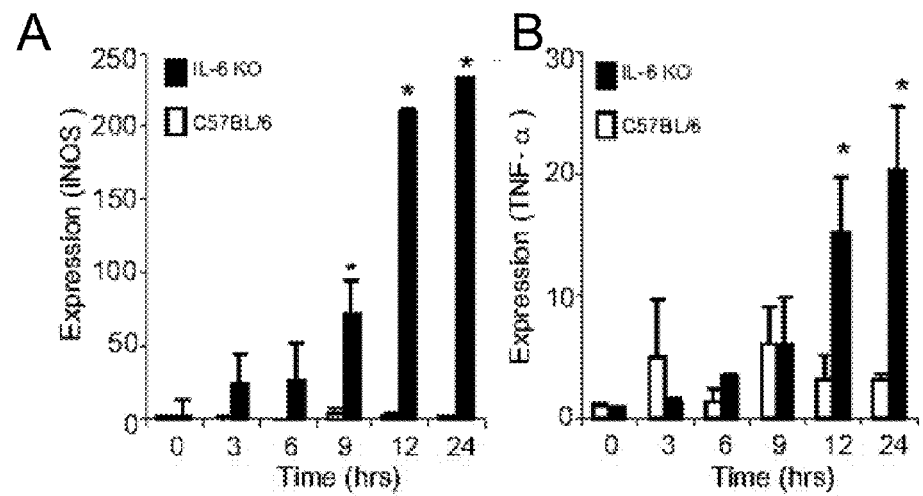
Figs. 13A-B
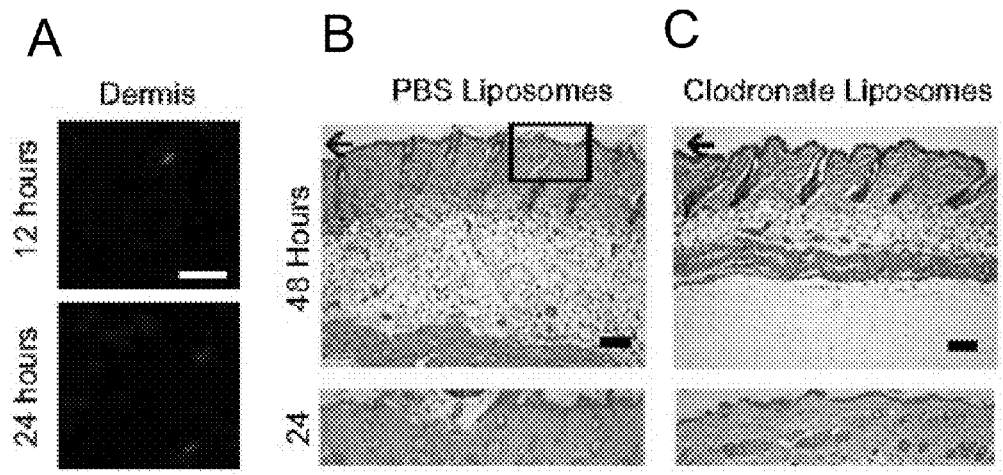
Figs. 14A-C

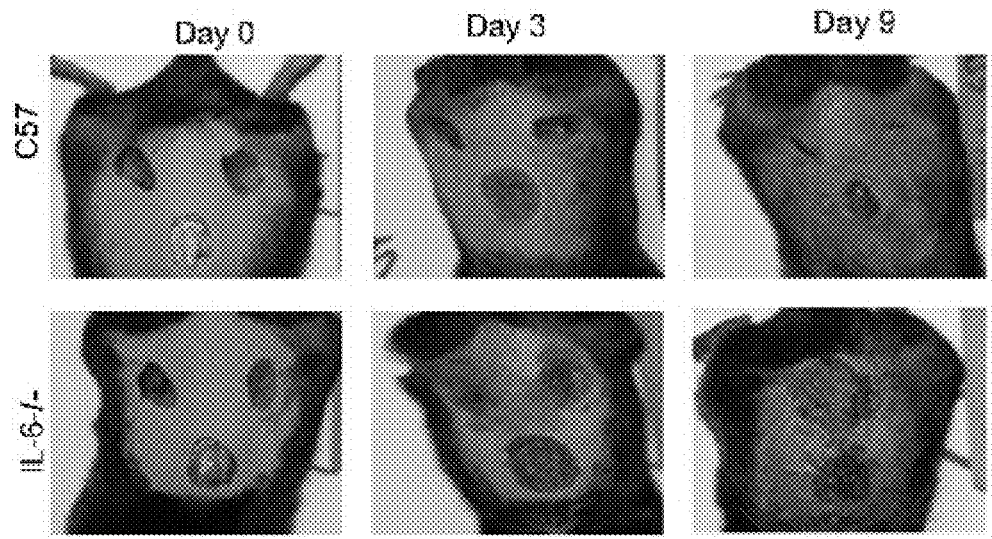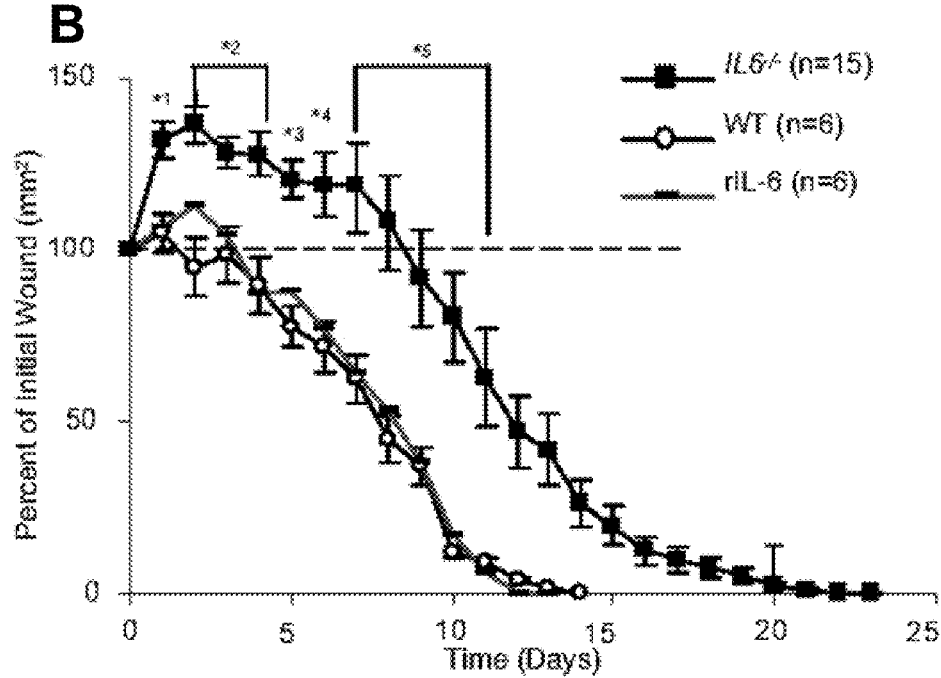
Figs. 15A-B

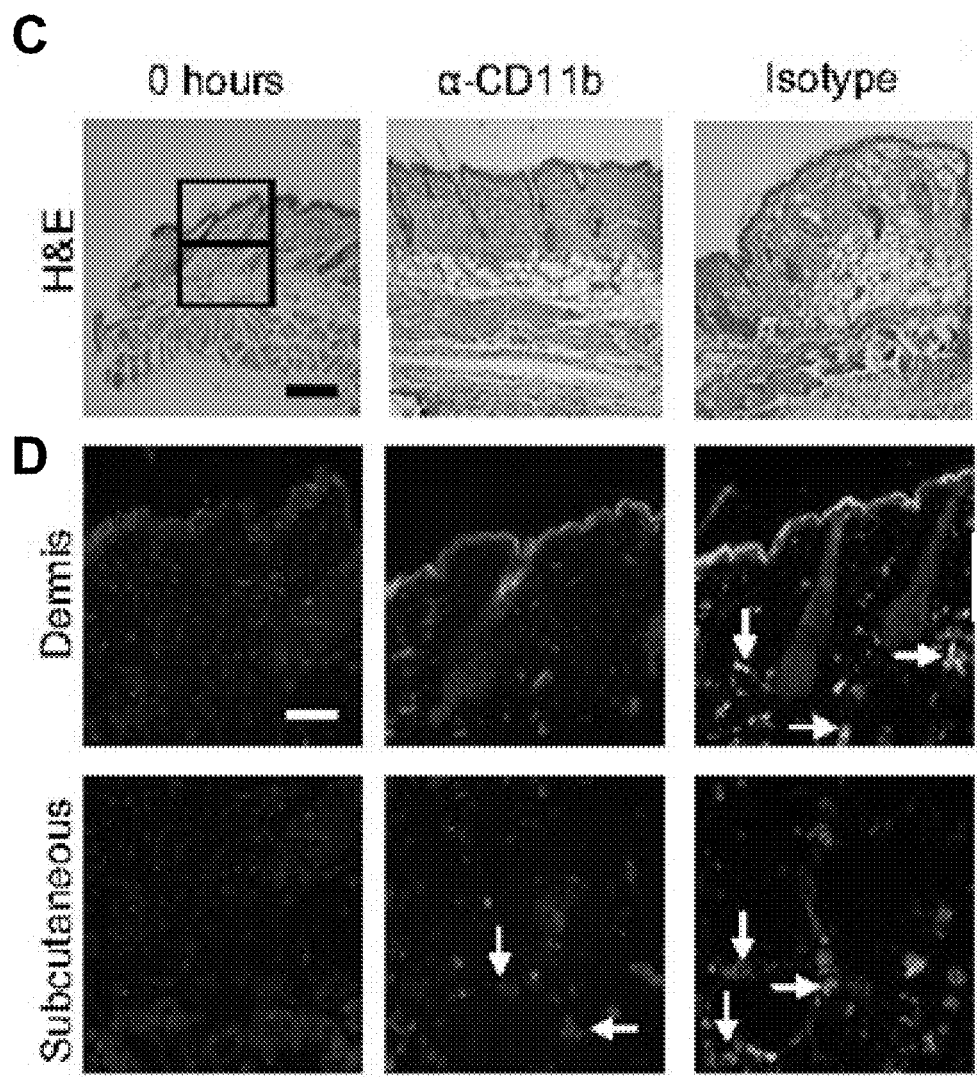
Figs. 15C-D

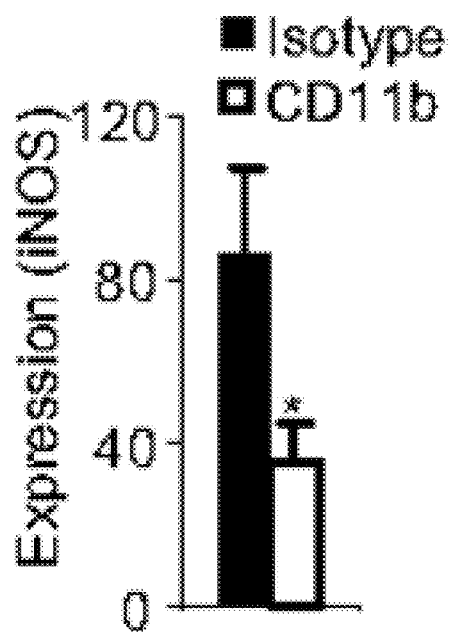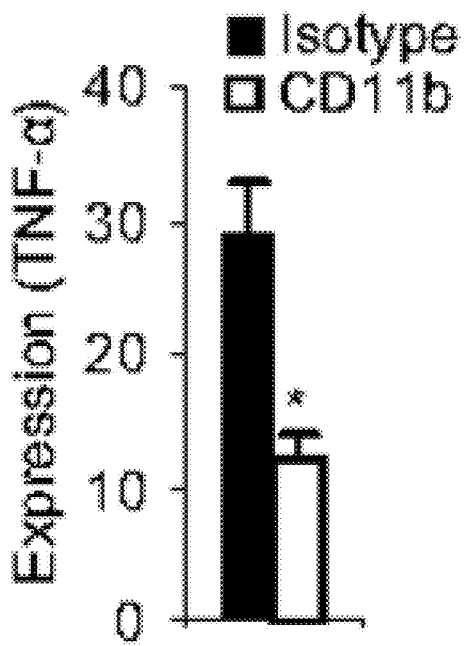
Figs. 16A-B

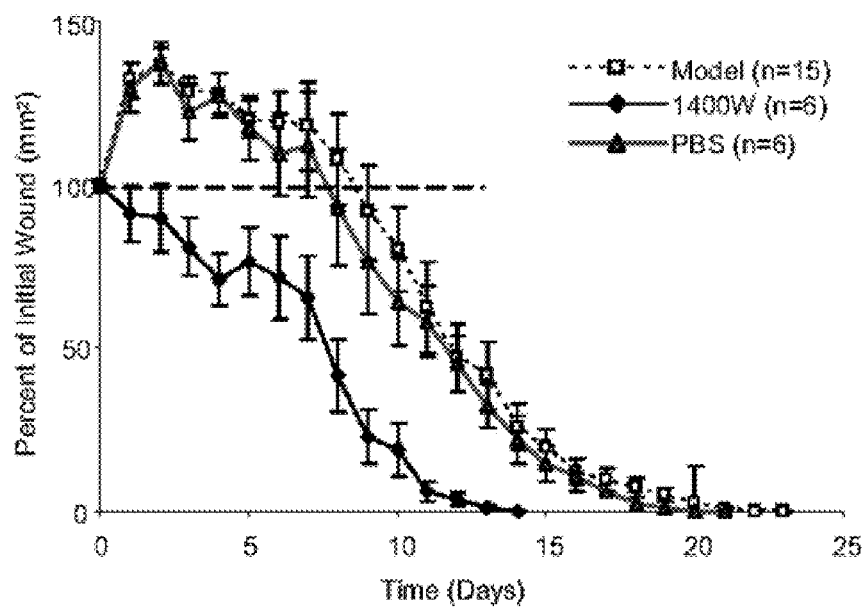
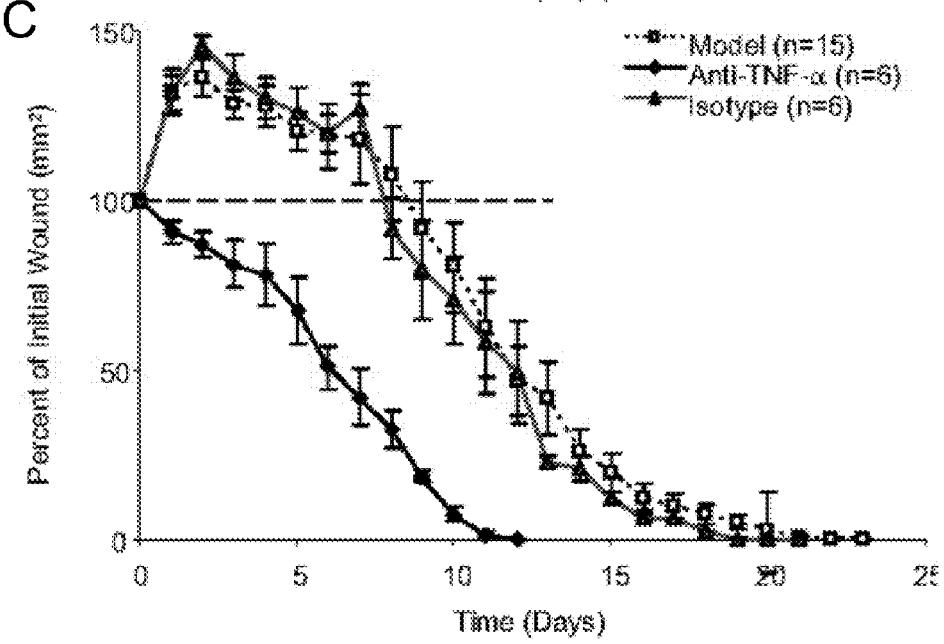
Figs. 17B-C

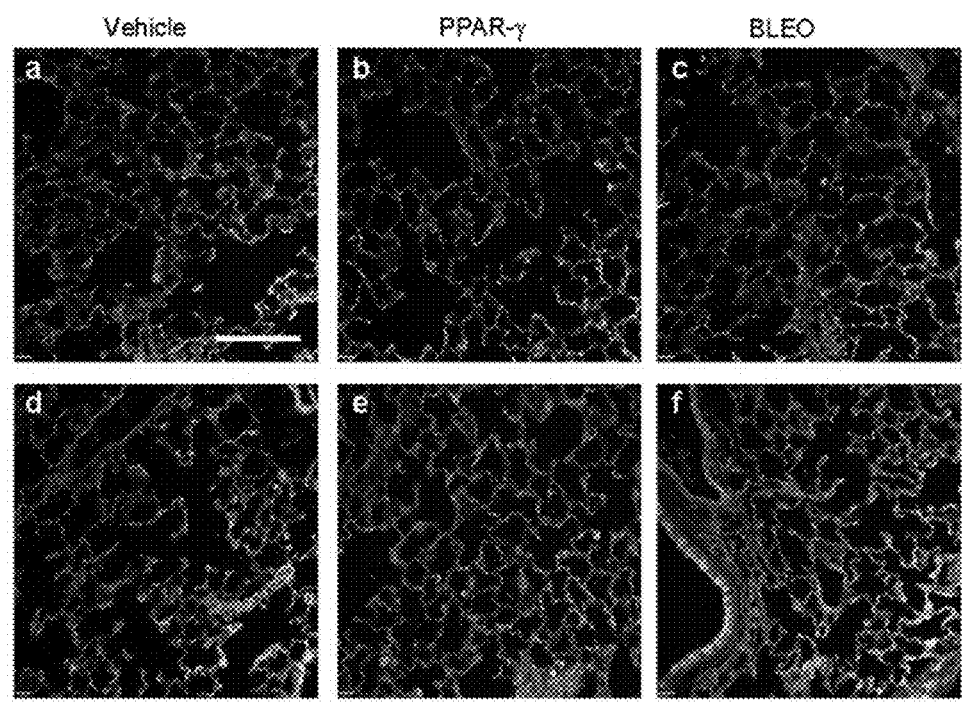
Figs. 18A-F

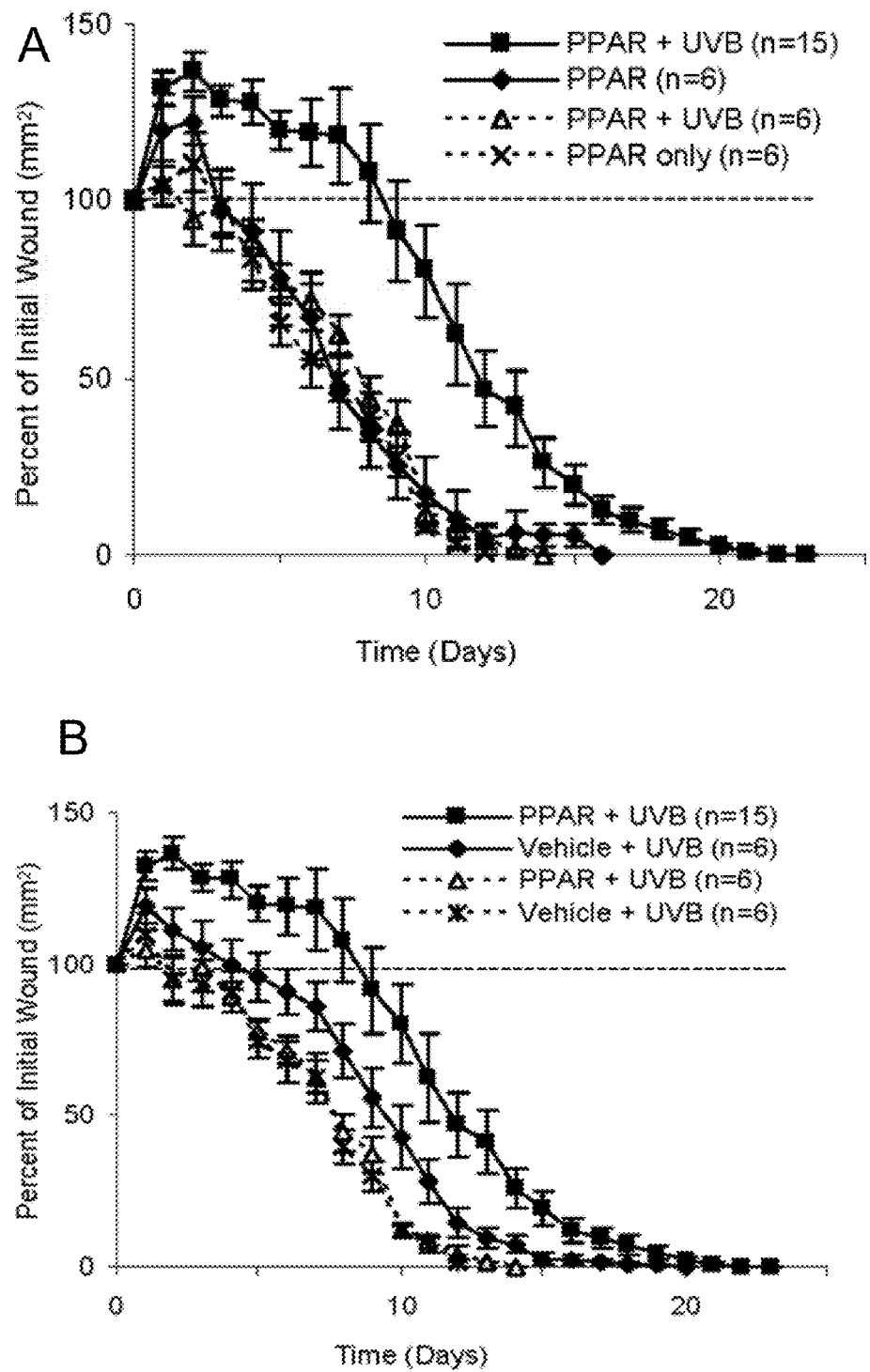
Figs. 19A-B

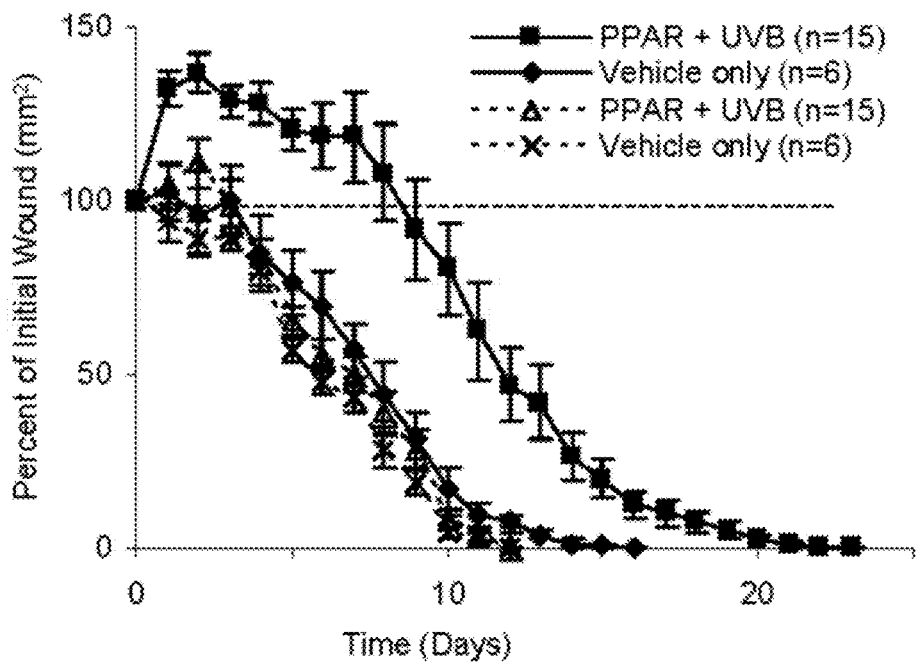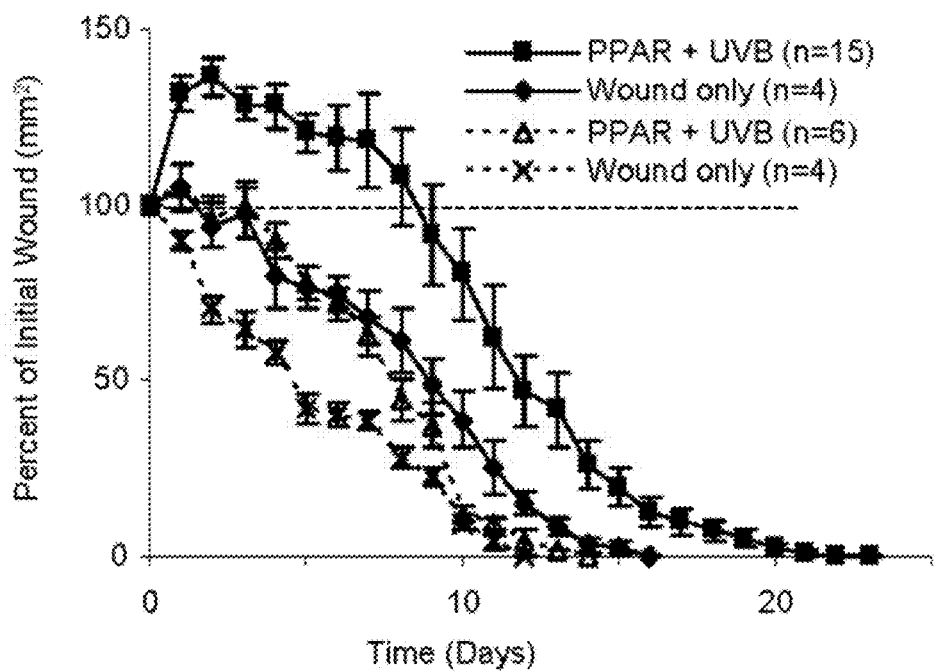
Figs. 19C-D

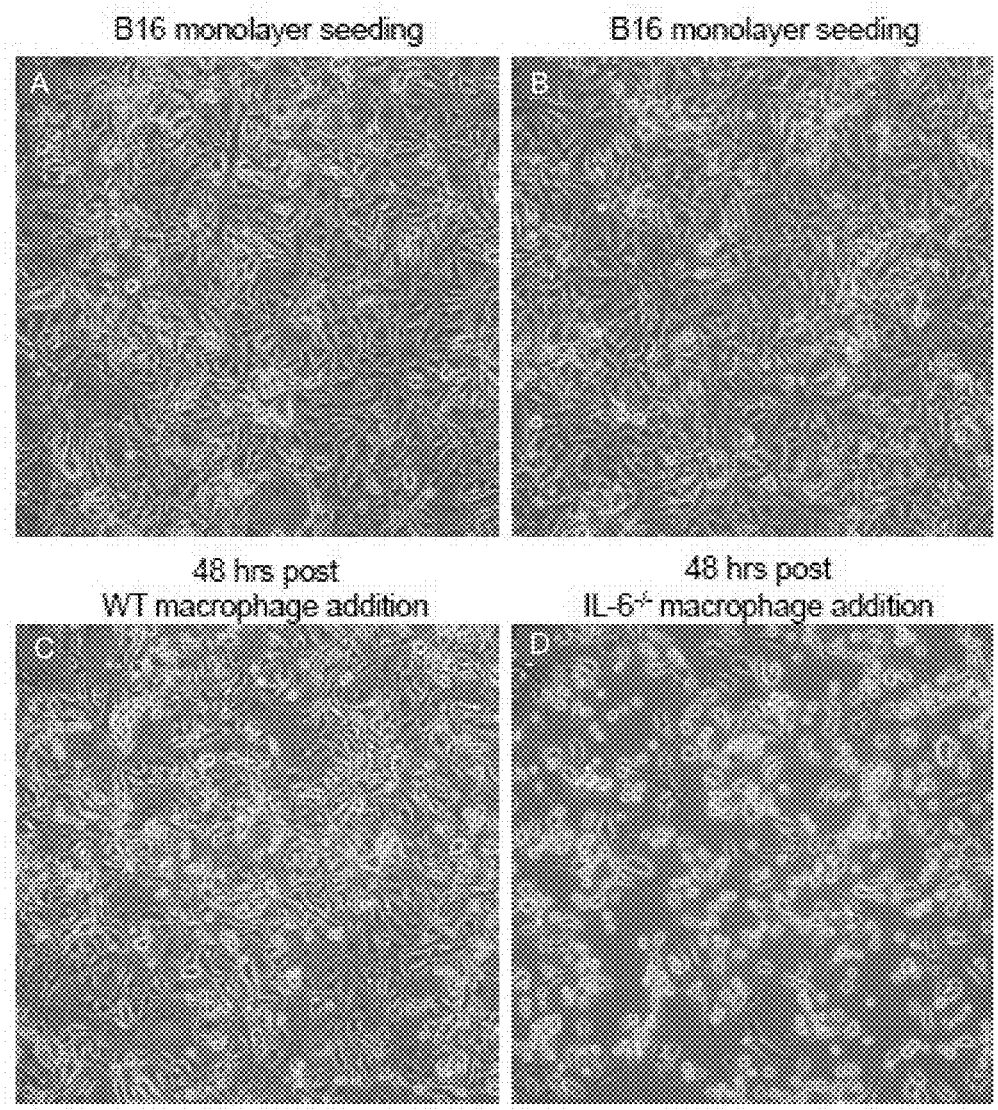
Fig. 24A-D

METHODS OF GENERATING HYPER INOS EXPRESSING CELLS AND USES THEREOF

RELATED APPLICATION

This application is a Continuation of U.S. application Ser. No. 13/578,785, filed Aug. 13, 2012, which is a National Phase filing of PCT/US2011/024757, filed Feb. 14, 2011, and claims priority from U.S. Provisional Application No. 61/303,871, filed Feb. 12, 2010, 61/320,879 filed Apr. 5, 2010, 61/434,151, filed Jan. 19, 2011, the subject matter of which are incorporated herein by reference in their entirety.

GOVERNMENT FUNDING

This invention was made with government support under Grant No. RR024990 awarded by The National Institute of Health. The United States government has certain rights to the invention.

TECHNICAL FIELD

This application relates to the generation of hyper iNOS (HiNOS) expressing myeloid cells and their use in therapeutic methods, methods of inhibiting wound healing, and an animal model of delayed wound healing.

BACKGROUND

Monocytes/macrophages demonstrate topographical and functional specificity directed by the micro-anatomic milieu suggesting a key role of extracellular factors in determining cell differentiation and functional activity. Interactions with the microenvironment results in macrophage activation, production of numerous soluble signaling molecules including pro- and anti-inflammatory cytokines, and growth and regulatory factors. Following injury, macrophages and monocytes are recruited and become key mediators of inflammation, tissue repair, and cellular debris clearance. However, dysfunctional control of the magnitude and duration of inflammation can result in damage to the host, such as in autoimmunity, numerous destructive and degenerative diseases (rheumatoid arthritis and Alzheimer's disease), non-healing ulcers, and infections such as leprosy and leishmaniasis. A hallmark of excess inflammation is damage to the surrounding tissue. However, the factors and underlying mechanisms that govern the function of macrophages in the context of inflammation and tissue destruction remain incompletely understood.

SUMMARY

An aspect of the application relates to a method of generating a hyper iNOS expressing cell. The method includes administering to a myeloid derived cell an amount of a PPARγ agonist and an IL-6/STAT3 signaling pathway antagonist effective to substantially inhibit STAT3 activation in the cell, and administering an inflammatory insult to the cell to stimulate hyper iNOS expression from the cell.

Another aspect of the application relates to a method of mediating local destruction of tissue in a subject. The method includes administering an amount of a PPARγagonist and an IL-6/STAT3 signaling pathway antagonist to macrophages of the subject effective to substantially inhibit STAT3 activation in the macrophages of the subject; and administering an amount of an inflammatory or damaging insult to the tissue of the subject effective to induce hyper iNOS expression of the macrophages in or about the periphery of the tissue.

A further aspect of the application relates to a method of treating cancer or a tumor in a subject. The method includes administering an amount of a PPARγ agonist and an IL-6/STAT3 signaling pathway antagonist to the subject effective to substantially inhibit STAT3 activation in macrophages of the subject; and administering an amount of an inflammatory or damaging insult to the cancer or tumor of the subject effective to induce hyper iNOS expression of the macrophages in or about the periphery of the cancer or tumor.

A still further aspect of the application relates to a method of treating an infection in a subject. The method includes administering an amount of a PPARγ agonist and an IL-6/STAT3 signaling pathway antagonist to macrophages of the subject effective to substantially increase iNOS expression of macrophages at the site of infection.

Yet another aspect of the application relates to a method for inhibiting unwanted wound repair in a subject. The method includes administering an amount of a PPARγ agonist and an IL-6/STAT3 signaling pathway antagonist to the subject effective to substantially increase iNOS expression of macrophages at the subject's wound.

BRIEF DESCRIPTION OF THE DRAWINGS

FIG. 1 illustrates schematic representations of mechanisms modulating inflammatory responses in (A) normal macrophages and (B), in the absence of IL-6, in hyper-inflammatory macrophages.

FIG. 2 illustrates graphs showing (A) iNOS expression and (B) TNF-α expression of bone marrow derived macrophages (BMDMs) isolated from C57BL/6 and IL6$^{-/-}$ mice stimulated with PPARγ agonist and/or LPS.

FIG. 3 illustrates graphs showing (A) iNOS expression and (B) TNF-α expression of in vivo elicited peritoneal macrophages isolated from C57BL/6 and IL6$^{-/-}$ mice stimulated with PPARγ agonist and/or LPS.

FIG. 4 illustrates graphs showing (A) iNOS expression and (B) TNF-α expression of in vivo elicited peritoneal macrophages treated with either rosiglitazone (Rosi) or Pioglitazone (Pio).

FIG. 5 illustrates a graph showing iNOS expression of in vivo elicited peritoneal macrophages treated with either rosiglitazone (Rosi) or an inhibitor of PPARγ signaling, GW9662.

FIG. 6 illustrates graphs showing (A) iNOS expression and (B) TNF-α expression of mice subjected to intratracheal bleomycin or treated with PPARγ agonist.

FIG. 7 illustrates (A) a graph showing the ratio of NFκBp65 to STAT3 after LPS stimulation with and without PPARγ agonist treatment and (B) a Western blot of NFκBp65 and STAT3 proteins extracted at 30 mins and 60 mins from WT and IL6$^{-/-}$ peritoneal macrophages.

FIG. 8 illustrates graphs showing (A) iNOS expression and (B) TNF-α expression from lungs of C57BL/6 and IL6$^{-/-}$ mice subjected to intratracheal bleomycin or treated with PPARγ agonist.

FIG. 9 illustrates confocal images of immunostaining for colocalization of iNOS with macrophage markers CD11b$^+$ & F4/80$^+$ in (A) wildtype and (B) IL6$^{-/-}$ mice lung sections.

FIG. 10 illustrates graphs showing (A) iNOS expression and (B) TNF-α expression from lungs of C57BL/6 and IL6$^{-/-}$ mice subjected to a cutaneous wounding protocol and treated with PPARγ agonist.

FIG. 11 illustrates confocal images of immunostaining for colocalization of iNOS with CD11b+ & F4/80+ cells in (A) C57BL/6 and (B) IL6−/− skin sections.

FIG. 12 illustrates images showing H&E staining of wild-type (A) C57B1/6 and (B) IL6−/− mice skin tissue surrounding the wound margin at 0, 9, and 24 hours following wounding; (C) confocal images of immunostaining for F4/80 and CD11b double positive cells in C57B1/6, and (D), IL6−/− mice skin sections.

FIG. 13 illustrates graphs showing (A) iNOS expression and (B) TNF-α expression during time course of wildtype C57B1/6 and IL6−/− mice skin tissue.

FIG. 14 illustrates images showing (A) iNOS staining colocalized with F4/80+ cells, but not with LY6/GR1+ cells, and H&E staining of skin after (B) PBS- or (C) clodronate-filled liposomes were injected intradermally surrounding the wound edge in IL6−/− mice.

FIG. 15 illustrates (A) images showing wounds of mice subjected to a wounding protocol including Application of a PPARγ agonist on IL6−/− animals; (B) a wound healing graph showing the mean percent of initial wound; (C) images showing H&E staining of wounded skin with and without anti-CD11b or isotype control i.p. injection; and (D) confocal images of immunostaining for F4/80, CD11b, and nucleus. Arrows indicate double positive cells.

FIG. 16 illustrates graphs showing (A) iNOS expression and (B) TNF-γ expression of skin surrounding the wound edge of IL6−/− mice.

FIG. 18 illustrates images showing (A-C) WT and (D-F) IL-6−/− mice lungs harvested and stained for CD11b, F4/80 markers of macrophages, and iNOS.

FIG. 19 illustrates graphs showing PPARγ agonist treatment of IL-6−/− mice delays wound healing and increases iNOS expression in skin. Wounds of IL-6−/− mice expand above 100% after treatment and remain above baseline after treatment with PPARγ agonist and UVB compared to the wounds of wildtype or IL-6−/− mice treated with (A) PPARγ agonist only; (B) UVB and vehicle; (C) vehicle only; and (D) wound only.

FIG. 24 illustrates images of (A, B) B16 melanoma cells seeded for 24 hours prior to introduction of either WT or IL-6−/− macrophages at a 4:1 E:T ratio of 2 million macrophages (pre-condition with PPARγ agonists and stimulated with LPS) to 500,000 melanoma cells, (C) 48 hours after co-seeding melanoma with the WT macrophages, and (D) 48 hours after co-seeding the melanoma with IL-6−/− macrophages revealed a drastic reduction of tumor cells.

DETAILED DESCRIPTION

Figure 17A:
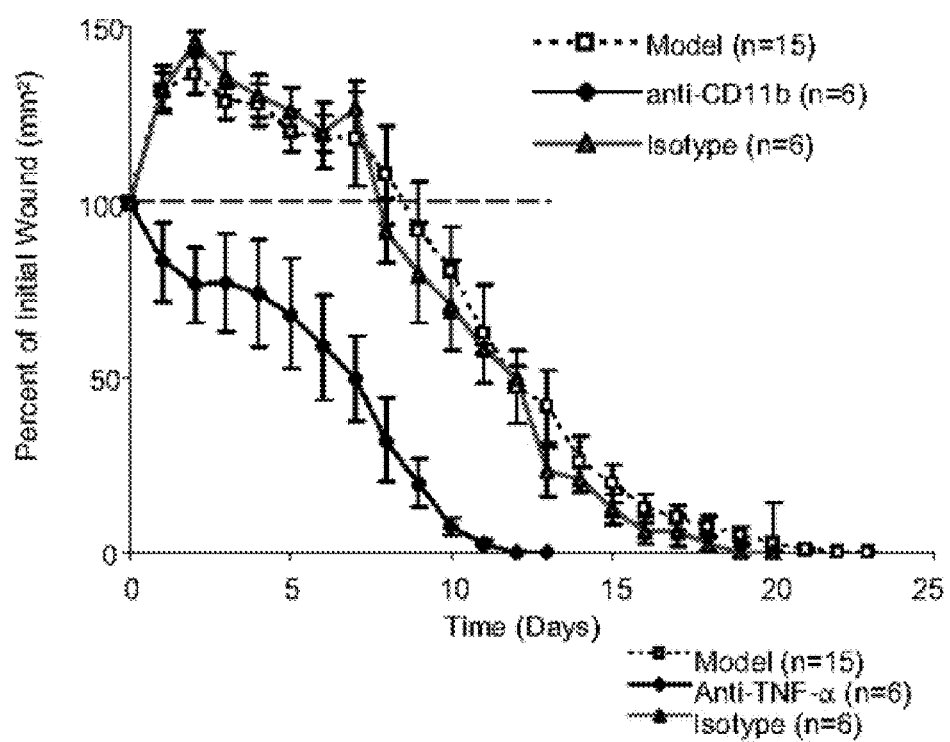
FIG. 17 illustrates wound healing graphs showing restored wound healing capacity of IL6−/− mice under experimental conditions when (A) treated with anti-CD11b to prevent monocyte/macrophage infiltration, (B) treated with the iNOS specific inhibitor, 1400 W, or (C) treated with an anti-TNF-γ antibody administered by i.p. injection 1 hour before wounding.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present application pertains. Commonly understood definitions of molecular biology terms can be found in, for example, Lodish et al., *Molecular Cell Biology*, 6th Edition, W. H. Freeman: New York, 2007, and Lewin, *Genes IX*, Jones and Bartlett Publishers: Mass., 2008. For convenience, certain terms employed in the specification, examples, and appended claims are collected here.

As used herein, "one or more of a, b, and c" means a, b, c, ab, ac, bc, or abc. The use of "or" herein is the inclusive or.

As used herein, "protein" is a polymer consisting of the 20 amino acids. Although "polypeptide" is often used in reference to relatively large polypeptides, and "peptide" is often used in reference to small polypeptides, usage of these terms in the art overlaps and is varied.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into a target tissue (e.g., the central nervous system), such that it enters the animal's system and, thus, is subject to metabolism and other like processes, for example, subcutaneous administration.

As used herein, the term "agent" or "drug" is used herein to denote a chemical compound, a mixture of chemical compounds, a biological macromolecule, or an extract made from biological materials such as bacteria, plants, fungi, or animal particularly mammalian) cells or tissues that are suspected of having therapeutic properties. The agent or drug may be purified, substantially purified or partially purified. As used herein, the term "purified" or "to purify" refers to the removal of one or more contaminants from a sample. As used herein, the term "partially purified" refers to the removal of a moderate portion of the contaminants of a sample to the extent that the substance of interest is recognizable by techniques known to those skilled in the art as accounting for a measurable amount of the mixture. Preferably, the compound of interest is at least 5% of the total preparation and up to 50% of the total preparation. As used herein, the term "substantially purified" refers to the removal of a significant portion of the contaminants of a sample to the extent that the substance of interest is recognizable by techniques known to those skilled in the art as the most abundant substance in the mixture.

As used herein, the term "therapeutically effective amount" refers to that amount of a composition, which results in amelioration of symptoms or a prolongation of survival in a patient. A therapeutically relevant effect relieves to some extent one or more symptoms of a disease or condition or returns to normal either partially or completely one or more physiological or biochemical parameters associated with or causative of the disease or condition.

As used herein "agonist" refers to molecules or compounds which mimic the action of a "native" or "natural" compound. Agonists may be homologous to these natural compounds in respect to conformation, charge or other characteristics. Thus, agonists may be recognized by, e.g., nuclear receptors. This recognition may result in physiologic and/or biochemical changes within the cell, such that the cell reacts to the presence of the agonist in the same manner as if the natural compound was present.

As used herein "antagonist" refers to molecules or compounds which decrease or inhibits the expression and/or function of a "native" or "natural" compound. An antagonist may be a type of receptor ligand or drug (e.g., a receptor antagonist) that does not provoke a biological response itself upon binding to a receptor at an active site or to allosteric sites on receptors, or they may interact at unique binding sites not normally involved in the biological regulation of the receptor's activity, but blocks or dampens agonist-mediated responses.

As used herein, the term "PPARγ agonist" refers to a compound or composition, which when combined with peroxisome proliferator-activated receptor gamma (PPARγ), directly or indirectly stimulates or increases an in vivo or in vitro reaction typical for the receptor (e.g., transcriptional regulation activity). The increased reaction can be measured by any of a variety of assays known to those skilled in the art. An example of a PPARγ agonist is a thiazolidinedione compound, such as troglitazone, rosiglitazone, pioglitazone, ciglitazone, WAY-120,744, englitazone, AD 5075, darglitazone, and congeners, analogs, derivatives, and pharmaceutically acceptable salts thereof.

As used herein, the term "IL-6/STAT3 signal pathway antagonist" refers to any agent that substantially decreases or inhibits the expression and/or function of a component of the IL-6/STAT3 signaling pathway in a myeloid cell.

As used herein, the term "IL-6 antagonist" refers to any agent that substantially decreases the expression and/or function of IL-6 in a subject. An example of an IL-6 antagonist is a statin.

As used herein, the term "subject" refers to any mammal, such as human beings, rats, mice, cats, dogs, goats, sheep, horses, monkeys, apes, rabbits, cattle, etc. The mammalian subject can be in any stage of development including adults, young animals, and neonates. Mammalian subjects can also include those in a fetal stage of development. Typically, the terms "patient" and "subject" are used interchangeably herein in reference to a human subject.

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

"Treating" or "treatment" of a condition or disease includes: (1) preventing at least one symptom of the conditions, i.e., causing a clinical symptom to not substantially develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. Treatment, prevention and ameliorating a condition, as used herein, can include, for example decreasing or eradicating a deleterious or harmful condition associated with unwanted wound repair, unwanted tissue, pathogenic infection, neoplasia, inflammation, and delayed wound healing.

As used herein, the term "promoting wound healing" or "promoting healing of a wound" mean augmenting, improving, increasing, or inducing closure, healing, restoring normal wound healing or repair of a wound.

This application relates to immunotherapeutic methods of promoting a robust innate immune response in a subject. This application also relates to the use of a subject's innate immunity to combat infection, unwanted tissue, and neoplastic disease through the selective generation of highly inflammatory hyper iNOS expressing myeloid cells (HiNOS). The HiNOS cells in accordance with the application can be generated through combinatory stimulation of a myeloid cell's PPARγ receptors and inhibition of the IL-6/STAT3 signaling pathway in the presence of an inflammatory or damaging insult or signal.

It was found that treatment of myeloid cells (or myeloid derived cells) with a PPARγ agonist in combination with inhibition of the IL-6/STAT3 signaling pathway in vitro and in vivo results in synergistic hyper-inflammatory responses, generation of pro-inflammatory, hyper-iNOS and TNF-γ expressing macrophages, and drastic macrophage-mediated de novo tissue destruction. The net response of PPARγ ligand exposure and concomitant IL-6 deficiency primes the myeloid cells so that during a period of stimulation, such as an inflammatory or damaging insult, the primed cells hyper express iNOS.

As illustrated schematically in FIG. 1A, monocytes and macrophages infiltrating inflamed tissue are exposed to the proinflammatory cytokine TNF-α which in turn activates NF-κB signaling resulting in induction of iNOS. To limit excessive exposure to TNF-α, cells release soluble TNF receptor, shielding them from excess stimulation and further NF-κB activation, a response that is diminished in cells deficient in IL-6. The addition of a PPARγ ligand, such as a thiazolidinedione, alters another aspect of NF-κB activity, specifically STAT3-mediated transrepression of NF-κB. As illustrated schematically in FIG. 1B, inhibition of STAT3 activation decreases its nuclear accumulation and in turn reduces its ability to control the magnitude of NF-κB responsive genes, such as iNOS. We found that excessive inflammation propagated by these HiNOS macrophages resulting in tissue destruction and ultimately leads to necrosis and delayed tissue repair as often seen in human chronic wounds. The HiNOS macrophages can be induced in several model systems suggesting that these findings are clinically relevant to a large number of patients, given the common concurrence of relative states of IL-6 inhibition with PPARγ activation induced either by pharmacologic agonists or by endogenous ligands generated during inflammation and oxidant stress.

One aspect of the application, therefore relates to a method of generating HiNOS cells. The method includes administering to a myeloid derived cell an amount of a PPARγ agonist and an IL-6/STAT3 signaling pathway antagonist effective to substantially inhibit STAT3 activation in the myeloid cell in combination with administering an inflammatory insult or signal to the myeloid cell to stimulate hyper iNOS expression from the cell. By substantially inhibiting STAT3 activation, it is meant the STAT3 activation in the myeloid derived cell treated with the PPARγ agonist and the IL-6/STAT3 signaling pathway antagonist is inhibited at least 10%, at least 20%, at least 30%, at least 40%, at least 50%, at least 60%, at least 70%, at least 80%, or at least 90% compared to untreated myeloid cells under similar in vivo or in vitro environmental or physiological conditions. The myeloid derived cell can be, for example, a macrophage or monocyte and the iNOS expression can be increased at least 2 fold, at least 5 fold, at least 10 fold, at least 20 fold, at least 30 fold, at least 40 fold, or at least 50 fold compared an untreated myeloid derived cell.

In some aspects, HiNOS cells can be generated in vitro. Myeloid cells for generating HiNOS cells in vitro can be obtained from bone marrow, peritoneal, bronchial lavage, and hepatic sources. In one non-limiting example, bone marrow derived macrophages can be harvested from a subject's femur using well known methods. Macrophages can then be isolated and cultured in vitro with the addition of macrophage-colony stimulating factor (MCSF). The cells can then stimulated with an inflammatory insult, such as by administering LPS, anti-CD11b antibody, or complement proteins, in combination with administration of a PPARγ agonist and an IL-6/STAT3 signaling pathway antagonist.

In some aspects, in vitro generated HiNOS cells derived from a subject can be administered back to the subject in a therapeutic method. For example, in vitro generated HiNOS cells can be administered systemically or implanted in a region of interest depending on the therapeutic purpose.

In other aspects of the application, HiNOS cells can be generated in vivo. For example, a subject can be administered a PPARγ agonist and an IL-6/STAT3 signaling pathway antagonist to substantially inhibit STAT3 activation in myeloid cells (e.g., macrophages) of the subject and the macrophages treated with the PPARγ agonist and an IL-6/STAT3 signaling pathway antagonist can be stimulated with an inflammatory or damaging insult to induce hyper iNOS expression from the cells.

In certain embodiments, the IL-6/STAT3 signaling pathway antagonist can include any agent or composition that substantially decreases or inhibits the expression and/or functional activity of a component of the IL-6/STAT3 signaling pathway in a myeloid cell. The functional activity of the IL-6/STAT3 signaling pathway can be suppressed, inhibited, and/or blocked in several ways including: direct inhibition of the activity of IL-6 and/or STAT3 (e.g., by using neutralizing antibodies, small molecules or peptidomimetics, dominant negative polypeptides); inhibition of genes that express IL-6 and/or STAT-3 (e.g., by blocking the expression or activity of the genes and/or proteins); activation of genes and/or proteins that inhibit one or more of the functional activity of IL-6 and/or STAT3 (e.g., by increasing the expression or activity of the genes and/or proteins); inhibition of genes and/or proteins that are downstream mediators of the iNOS expression (e.g., by blocking the expression and/or activity of the mediator genes and/or proteins); introduction of genes and/or proteins that negatively regulate one or more of functional activity of IL-6 and/or STAT3 (e.g., by using recombinant gene expression vectors, recombinant viral vectors or recombinant polypeptides); or gene replacement with, for instance, a hypomorphic mutant of STAT-3 (e.g., by homologous recombination, overexpression using recombinant gene expression or viral vectors, or mutagenesis).

In an embodiment of the application, the IL-6/STAT3 signaling pathway antagonist is an IL-6 antagonist. In some aspects, the IL-6 antagonist can include a humanized IL-6 receptor-inhibiting monoclonal antibody. In certain aspects, the IL-6 antagonist is the product tocilizumab (a descriptive name sold under the trademark ACTEMRA® by Roche, Switzerland). In other aspects, the IL-6 antagonist can include a vaccine that when administered to a subject generates IL-6 antibodies in the subject. An example of such a vaccine is disclosed in Fosergau et al. Journal of Endocrinology (2010) 204, 265-273.

In another embodiment, the IL-6/STAT3 signaling pathway antagonist is a tyrosine kinase inhibitor. Exemplary tyrosine kinase inhibitors for use in the present invention include but are not limited to tyrphostins, in particular AG-490, and inhibitors of Jak, Src, and BCR-Abl tyrosine kinases. Other tyrphostins suitable for use herein include, but are not limited to AG17, AG213 (RGS0864), AG18, AG82, AG494, AG825, AG879, AG1112, AG1296, AG1478, AG126, RG13022, RG14620, AG555, and related compounds. In certain aspects, a BCR-Abl tyrosine kinase inhibitor for use herein can include the product imatinib mesilate (a descriptive name sold under the trademark GLEEVEC® by Novartis, Switzerland).

In a further embodiment, the IL-6/STAT3 signaling pathway antagonist is an HMG CoA reductase inhibitor (3-hydroxymethylglutaryl coenzyme A reductase inhibitors) (e.g., statin). HMG-CoA (3-hydroxy methylglutaryl coenzyme A) reductase is the microsomal enzyme that catalyzes the rate limiting reaction in cholesterol biosynthesis (HMG-CoA Mevalonate). Statins can inhibit and/or reduce IL-6 expression when administered to myeloid cells (e.g., macrophages) and as shown in Examples 3 and 4 can be used in combination with PPARγ agonists to generate hyper-INOS expressing macrophages.

Statins that can be used for administration, or co-administration with other agents according to the invention include, but are not limited to, simvastatin (U.S. Pat. No. 4,444,784), mevistatin, lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622, 985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302, 604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116, 870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994, 494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860 U.S. Pat. No. 4,940,800, U.S. Pat. No. 4,940,727, U.S. Pat. No. 4,939,143, U.S. Pat. No. 4,929, 620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

In yet another embodiment, the IL-6/STAT3 signaling pathway antagonist can be a STAT3 inhibitor. Examples of STAT3 inhibitors are described in U.S. Patent Application No. 2010/0041685 and can include 4-[3-(2,3-dihydro-1,4-benzodioxin-6-yl)-3-oxo-1-propen-1-yl]benzoic acid; 4-{5-[(3-ethyl-4-oxo-2-thioxo-1,3-thiazolidin-5-ylidene]methyl]-2-fu-ryl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene) methyl]-6--ethoxyphenoxy}methyl)benzoic acid; methyl 4-({[3-(2-methyoxy-2-oxoethyl)-4,8-dimethyl-2-oxo-2H-chromen-7-yl]oxy}met-hyl)benzoate; 4-chloro-3-{5-[(1,3-diethyl-4,6-dioxo-2-thioxotetrahydro-5(2H)-pyrimidiny-lidene)methyl]-2-furyl}benzoic acid; a functionally active derivative thereof and a mixture thereof. Other examples of STATS inhibitors are described in WO 2010/118309 and in G. Zinzalla et al. Bioorg. Med. Chem. Lett. 20 (2010)7029-7032.

In certain embodiments, the PPARγ agonist can include any agent or composition that substantially increases or promotes the activation and/or functional activity of PPARγ. The functional activity of the PPARγ can be increased or promoted in several ways including: direct activation of PPARγ with an endogenous PPARγ ligand (e.g., by using small molecules or peptidomimetics); up regulation of genes for ligands of PPARγ (e.g., by promoting the expression or activity of the genes and/or proteins); activation of genes and/or proteins that promote one or more of the functional activity of PPARγ (e.g., by increasing the expression or activity of the genes and/or proteins); promotion of genes and/or proteins that are downstream mediators of PPARγ activation; and introduction of genes and/or proteins that promote one or more of functional activity of PPARγ (e.g., by using recombinant gene expression vectors, recombinant viral vectors or recombinant polypeptides).

In other embodiments, PPARγ agonists that can be used herein include, for example, prostaglandin J2 (PGJ2) and analogs thereof (e.g., A2-prostaglandin J2 and 15-deoxy-2,4-prostaglandin J2), members of the prostaglandin D2 family of compounds, docosahexaenoic acid (DHA), and thiazolidinediones (e.g., ciglitazone, troglitazone, pioglitazone and rosiglitazone).

In some embodiments, the PPARγ agonist can include a thiazolidinedione or a derivative thereof. In some aspects, a PPARγ agonist for use in the present invention includes at least one compound or a pharmaceutically salt thereof selected from the group consisting of: (+)-5[[4-[(3,4-dihydro-6-hydroxy-2,5,7,8-tetramethyl-2H-1-benzopyran-2-yl)

methoxy]phenyl]methyl]-2,4-thiazolidinedione; 5-[4-[2-(5-ethylpyridin-2-yl)ethoxyl]benzyl]thiazolidine-2,4-dione; 5-[4-[(1-methylcyclohexyl)methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino]ethoxy]benzyl]-5-methlthiazolidine-2,4-dione; 5-[4-[2-[2,4-dioxo-5-phenylthiazolidine-3-yl]ethoxy]benzyl]thiazolidine-2,4-dione; 5-[4-[2-[(N-methyl-N-(phenoxycarbonyl)amino]ethoxy]benzyl]thiazolidine-2,4-dione; 5-[4-[2-phenoxyethoxy)benzyl]thiazolidine-2,4-dione; 5-[4-[2-(4-chorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl] thiazolidine-2,4-dione; 5-[(2-benzyl-2,3-dihydrobenzopyran)-5-ylmethyl]thiazolidine-2,4-dione; 5-[[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy] benzyl]thiazolidine-2,4-dione; 5-[4-[3-(5-methyl-2-phenyloxazol-4-yl)propionyl]benzyl]thiazolidine-2,4-dione; 5-[2-(5-methyl-2-phenyloxazol-4-ylmethyl)benzofuran-5-ylmethyl]oxazolidine-2,4-dione; 5-[4-[2-(N-methyl-N-(2-pyridyl)amino]ethoxy]benzyl]thiazolidine-2,4-dione; and 5-[4-[2-(N-(benzoxazol-2-yl)-N-methylamino]ethoxy]benzyl]oxazolidine-2,4-dione. In certain aspects, the PPARγ agonist is the product rosiglitazone (a descriptive name sold under the trademark AVANDIA® by GlaxoSmithKline, U.K.).

In other embodiments, PPARγ agonists can include, but are not limited to, L-tyrosine-based compounds, farglitazar, GW7845, indole-derived compounds, indole 5-carboxylic acid derivatives and 2,3-disubstituted indole 5-phenylacetic acid derivatives. It is significant that most of the PPARγ agonists exhibit substantial bioavailability following oral or topical administration and have little or no toxicity associated with their use (See, e.g., Saltiel and Olefsky, Diabetes 45:1661 (1996); Wang et al., Br. J. Pharmacol. 122:1405 (1997); and Oakes et al., Metabolism 46:935 (1997)).

PPARγ agonists that can be used for practicing the present invention, and methods of making these compounds, are disclosed in WO 91/07107; WO 92/02520; WO 94/01433; WO 89/08651; WO 96/33724; WO 97/31907; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; 5,260,445; 5,814,647; 5,902,726; 5,994,554; 6,294,580; 6,306,854; 6,498,174; 6,506,781; 6,541,492; 6,552,055; 6,579,893; 6,586,455; 6,660,716; 6,673,823; 6,680,387; 6,768,008; 6,787,551; 6,849,741; 6,878,749; 6,958,355; 6,960,604; 7,022,722; and U.S. Applications 20030130306, 20030134885, 20030109579, 20030109560, 20030088103, 20030087902, 20030096846, 20030092697, 20030087935, 20030082631, 20030078288, 20030073862, 20030055265, 20030045553, 1 20020169192, 20020165282, 20020160997, 20020128260, 20020103188, 20020082292, 20030092736, 20030069275, 20020151569, and 20030064935. The disclosures of these publications are incorporated herein by reference in their entireties, especially with respect to the PPARγagonists disclosed therein, which may be employed in the methods described herein.

The inflammatory or damaging insult used to induce hyper iNOS expression from the myeloid cells treated with or administered a PPARγ agonist and an IL-6/STAT3 signaling pathway antagonist can include any inflammatory or damaging insult that elicits an inflammatory response from the myeloid cells. For example, the inflammatory or damaging insult can include or be administered via trauma, physical stress, contact with a chemical, contact with biological agent, and/or exposure to radiation. Chemical insult in order to promote iNOS expression can include, for example, local or systemic exposure or contact with thioglycolate (peritoneum), bleomycin (lung), and $CCl_4$ (liver). Biological insult can include local or systemic exposure to an endotoxin, such as Lipopolysaccharides (LPS), a complement protein, ligands for a complement receptor, or an anti-CD11b antibody. Radiation can include local or systemic exposure to therapy or interventional radiation therapy or phototherapy, including but not limited to UV phototherapy, laser therapy, RF ablation therapy, external beam radiotherapy, brachytherapy, unsealed source radiotherapy, particle therapy, and radioisotope therapy. In certain aspects of the application, a physical insult to a subject's skin can include exposure to UV phototherapy or external beam radiotherapy.

It will be appreciated that the methods of the application are not limited to above-identified PPARγ agonists, IL-6/STAT3 signaling pathway antagonists, and inflammatory and damaging insults and that other identified PPARγ agonists, IL-6/STAT3 signaling pathway antagonists, and inflammatory and damaging insults can also be used.

It is contemplated that the accumulation of HiNOS cells in a region of interest and the hyper expression of iNOS in that region, results in local tissue destruction. Without being bound by theory, it is believed that a product of iNOS (e.g., superoxide, a precursor to peroxynitrite) can mediate the destruction of pathogens, and unwanted cells and tissue. In an embodiment of the application, an inflammatory or damaging insult can be administered directly to a site of infection or to a site of unwanted or diseased tissue previous, during, and/or following administration of the PPARγ agonist and an IL-6/STAT3 signaling pathway antagonist to myeloid cells, which are treated in vivo or administered to the subject after in vitro administration of the PPARγ agonist and an IL-6/STAT3 signaling pathway antagonist.

Another embodiment of the application therefore relates to a method of mediating local destruction of tissue in a subject. The method includes administering an amount of a PPARγ agonist and IL-6/STAT3 signaling pathway antagonist to myeloid cells (e.g., macrophages) of the subject effective to substantially inhibit STAT3 activation in myeloid cells in the subject. Prior to, during, and/or following administration of the a PPARγagonist and IL-6/STAT3 signaling pathway antagonist, the tissue can be subjected to an inflammatory or damaging insult to induce hyper iNOS expression in the myeloid cells that are in or about the periphery of the tissue and mediate local destruction of the tissue.

In one embodiment, the method can be used to mediate local destruction of neoplastic tissue. In the method, a therapeutically effective amount of a PPARγ agonist and an IL-6/STAT3 signaling pathway antagonist can be administered to myeloid cells of the subject, either systemically or locally, e.g., directly to or about the periphery of a subject's neoplastic tissue, to substantially inhibit STAT3 activation in the myeloid cells. An inflammatory or damaging insult can then be administered to the neoplastic tissue to induce hyper iNOS expression of the myeloid cells that are in or about the periphery of the neoplastic tissue and promote local destruction of the neoplastic tissue.

Neoplastic tissues that can be treated using the method of the application can include cancers or tumors including (but not limited to): leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the methods of the application can be used in the treatment of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated in the skin, lung, colon, rectum, breast, prostate, bladder, kidney, pancreas, ovary, or uterus. In other specific embodiments, sarcoma, melanoma, small lung carcinoma, or leukemia is treated.

In some embodiments, the cancer is malignant. In other embodiments, the disorder to be treated is a pre-cancerous condition. In specific embodiments, the pre-cancerous condition is high-grade prostatic intraepithelial neoplasia (PIN), fibroadenoma of the breast, or fibrocystic disease.

In certain embodiments, the inflammatory or damaging insult can be delivered to cancer cells by site-specific means. Cell-type-specific delivery can be provided by conjugating an inflammatory molecule to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

In certain embodiments, therapy by administration of one or more the PPARγ agonist and the IL-6/STAT3 signaling pathway antagonist can be combined with the administration of one or more therapies such as, but not limited to, chemotherapies, radiation therapies, hormonal therapies, and/or biological therapies/immunotherapies. Prophylactic/therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including, but not limited to, double-stranded or single-stranded DNA, or double-stranded or single-stranded RNA, as well as triple helix nucleic acid molecules. Prophylactic/therapeutic agents can be derived from any known organism (including, but not limited to, animals, plants, bacteria, fungi, and protista, or viruses) or from a library of synthetic molecules.

In certain embodiments, the neoplastic tissue can be cutaneous melanoma and non-melanoma skin cancer tissue. The method can include melanoma and non-melanoma skin cancer ablation, wherein the subject is administered a therapeutically effective amount of a PPARγ agonist and an IL-6/STAT3 signaling pathway antagonist before, during, or after surgical removal of a cancerous lesion in order to increase progression-free survival time.

In some aspects, the methods described herein are used in the treatment of pathogenic infection. It is contemplated that increasing the expression of iNOS by localized generation of HiNOS cells directly at or about the periphery of a site of infection can inhibit a pathogenic infection. For example, a therapeutically effective amount of a PPARγ agonist and an IL-6/STAT3 signaling pathway antagonist can be administered to the subject systemically or locally, e.g., directly to or about the periphery of pathogenic infection, in order to increase iNOS expressing cells at the site to mediate the destruction of a pathogenic organism.

It will be appreciated that the methods of application need not be limited to the treatment of pathological conditions or uses and can be used for cosmetic applications. For example, the methods described herein can be used for removal of scar tissue in a subject, wherein a therapeutically effective amount of PPARγ agonist and IL-6/STAT3 signaling pathway antagonist is administered to myeloid cells of the subject in combination with an inflammatory or damaging insult (e.g., UV radiation) directly to or about the periphery of the subject's scar tissue. In other examples, the methods described herein can be used for removal of a tattoo of a subject, unwanted hair, and/or an actinic keratosis lesion wherein a therapeutically effective amount of a PPARγ agonist and an IL-6/STAT3 signaling pathway antagonist is administered to myeloid cells of the subject in combination with an inflammatory or damaging insult (e.g., laser therapy or photorejuvenation) directly to or about the periphery of the tissue being treated (e.g., tattoo, hair follicle, skin).

The methods contemplated herein can also be used for inhibiting normal wound repair in a subject. The method includes administering a therapeutically effective amount of a PPARγ agonist and an IL-6 inhibitor to the subject. The therapeutically effective amount is the amount of PPARγ agonist and IL-6 inhibitor can substantially increase HiNOS expressing cells at or about the periphery of the wound of the subject. For example, the method may be used to inhibit adhesions in a subject (e.g., peritoneal adhesions) and scar formation (e.g., keloid formation, hypertrophic scarring, and striae).

Other embodiments of the application relate to pharmaceutical compositions including at least one PPARγ agonist and at least one IL-6/STATS signaling pathway antagonist described above. Pharmaceutical compositions described herein will generally include an amount of PPARγ agonists and IL-6/STAT3 signaling pathway antagonist admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

The dose, amount, and/or quantity of the pharmaceutical compositions described above which are administered to the subject can depend on the specific IL-6/STAT3 signaling pathway antagonist(s) and PPARγ agonist(s) selected. It will be appreciated that the dosage amounts used will depend on the potency of the specific PPARγ agonist and the therapeutic regimen employed.

In another aspect, the IL-6/STAT3 signaling pathway antagonist and PPARγ agonist when administered in combination to subject can be administered at an amount or dosage to achieve a therapeutic effect that is substantially less (i.e., subtherapeutic dose or amount) than the amount or dose that would be required to achieve a therapeutic effect if each compound was administered alone. Co-administration of the IL-6/STAT3 signaling pathway antagonist and PPARγ agonist to the subject can also mitigate resistance to one single agent. Such resistance results either in the requirement for higher dosages of the drug and/or the renewed symptoms.

Moreover, co-administration of IL-6/STAT3 signaling pathway antagonist and PPARγ agonist to the subject can mitigate toxicity and side effects associated with potentially administering a single agent at an amount effective to achieve a therapeutic effect. For example, according to an FDA alert issued on May 21, 2007, therapeutic doses of the PPARγ agonist rosiglitazone, are associated with a substantially increased risk of heart attack, and even higher risk of death from all cardiovascular diseases. In addition, both rosiglitazone and pioglitazone have been suspected of causing macular edema. Therefore, there is a practical upper limit to the amount that a subject can receive. However, if two or more agents are used in concert, the dosage of any single drug can be lowered. This is beneficial to the patient since using lower levels of therapeutic agents is generally safer for the patient. Additionally, cells are less likely to generate resistance to the combination of drugs as they are to a single drug. Thus, in some aspects of the present invention, the compositions described herein can be administered to a subject at a subtherapeutic level.

The method of the application is not limited by the order in which the agents are administered. In one embodiment, the agents are administered sequentially. In another embodiment, the agents are administered as a combined formulation (e.g., a formulation comprising an IL-6/STAT3 signaling pathway antagonist and a PPARγ agonist).

The agents described herein are not limited by the route of administration. For example, the pharmaceutical compositions may be administered orally, intravenously, intraperitoneally, or by direct intralesional injection. In some aspects of the present invention, pharmaceutical compositions may be administered directly to or about the periphery of a lesion or wound by injection, for example, under bronchoscopy, endoscopy, intra-operativley (e.g., during surgery) or as an adjuvant therapy, or in the case of dermatological disorders (e.g., skin cancer), for example, by direct application of creams or ointments. In certain aspects, one agent is administered by one route, while the second agent is administered by a second route.

The IL-6/STAT3 signaling pathway antagonist and PPARγ agonist can be formulated for systemic administration and/or topical administration. Advantageously, the IL-6/STAT3 signaling pathway antagonist and PPARγ agonist can be administered by local topical administration to a region of interest, for example, the site of an unwanted tissue. Topical administration is desirable because a lower dosage can be administered to the subject being treated to provide a therapeutically effective benefit. Additionally, administration of a lower topical dosage can mitigate adverse side-effects that may be associated with systemic administration.

Topical formulations include those for delivery via the mouth (buccal) and through the skin such that at least one layer of skin (i.e., the epidermis, dermis, and/or subcutaneous layer) is contacted with an IL-6/STAT3 signaling pathway antagonist and PPARγ agonist. Topical delivery systems may be used to administer topical formulations of the present invention. Topical delivery systems can include, for example, transdermal patches containing an IL-6/STAT3 signaling pathway antagonist and PPARγ agonist or derivative thereof to be administered. Delivery through the skin can further be achieved by iontophoresis or electrotransport, if desired.

Formulations for topical administration in the mouth can include any one or combination of: lozenges comprising an IL-6/STAT3 signaling pathway antagonist and PPARγ agonist in a flavored basis, usually sucrose and acacia or tragacanth; pastilles comprising an IL-6/STAT3 signaling pathway antagonist and PPARγ agonist in an inert basis such as gelatin and glycerin or sucrose and acacia; and mouthwashes comprising an IL-6/STAT3 signaling pathway antagonist and PPARγ agonist to be administered in a suitable liquid carrier.

Formulations for topical administration to the skin can include ointments, creams, gels, and pastes comprising IL-6/STAT3 signaling pathway antagonist and PPARγagonist to be administered in a pharmaceutically acceptable carrier. Topical formulations for administration to the skin can include creams, ointments, and gels, for example, and can be prepared using oleaginous or water-soluble ointment bases, as is well known to those in the art. For example, these formulations may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases may also be used including, for example, glycol ethers and derivatives, polyethylene glycols, polyoxyl 40 stearate, and polysorbates.

Other examples of topical delivery compositions that can be used for delivering the IL-6/STAT3 signaling pathway antagonist and/or PPARγagonist include polycosanol combinations and nanoparticulate aersol formulations described, for example, in U.S. Pat. Nos. 7,521,068 and 7,763,278.

Another aspect of the application relates to a method of generating an animal model of chronic delayed wound healing. The method includes the in vivo generation of HiNOS cells in an animal and the administration of a non-lethal wound. In some aspects, the animal is an IL-6$^{-/-}$ animal that has been wounded and administered a PPARγ agonist. However, it is contemplated that an IL-6/STAT3 signaling pathway antagonist described herein can be administered to an IL-6$^{+/+}$ animal.

In one exemplary embodiment, a delayed wound healing animal model is generated by shaving and depilating 6-8 week old female IL-6$^{-/-}$ mice a minimum of 3 days prior to experimentation. On day 0, the mice receive 3×6 mm punch biopsies on their dorsal side. Mice are then subjected to a low dose of ultraviolet radiation (e.g., 72 mJ/cm$^2$ UVB), and a topical PPARγ agonist is applied in a petrolatum. From there, topical PPARγ agonist is applied daily after wound size measurements are obtained.

In some aspects of the invention, an animal model is characterized by an increase in time for wound healing of at least about 50%, at least about 100%, at least about 150%, or at least about 200% compared to a control. An animal model can also be characterized by enlargement of a wound, failure to initiate wound healing with sustained enlarged wounds, and delayed complete re-epithieliazation compared to a control.

A model can be used to determine interventions and therapies to treat both acute and chronic delayed wounds. Therefore, the generation of model of delayed wound healing provides the means to study 1) mechanisms that delay wound repair and 2) clinically applicable therapies to increase the rate of healing.

The animal model can be employed in testing the efficacy of drug compounds aimed at treating delayed wound healing. For example, the animal model of the can be used in a method of identifying agents that stimulate wound repair and the healing of damaged tissue. The method includes administering a test compound to a mammal either before or after wound or damage is administered. A test compound can then be administered (e.g., via topical administration or injection). In one aspect, a test compound that causes a significant initiation of wound healing, decrease in the time of wound repair, and/or re-epithieliazation compared to a control is indicative of an effective agent.

In another example, the animal model can be used in a method of identifying an agent that inhibits unwanted wound healing. The method includes administering to a mammal a test compound either before or after wound or damage is administered. A test compound that causes significant delay or increase in the time of wound repair is indicative of an effective agent.

While hyper iNOS expression from HiNOS cells can be advantageous in some therapeutic applications, excessive nitric oxide (NO) production via induction of iNOS can lead to unwanted local tissue damage and has been implicated in numerous destructive inflammatory diseases, a delay in wound healing, and local destruction of tissue (destruction of hair follicles). Delayed wound healing can result from a sustained inflammatory state at the wound site. Thus, it is further contemplated by the application that agents that inhibit iNOS expression in a subject can be used to treat inflammatory disease and/or promote wound healing in a subject. Of particular relevance are subjects that have reduced IL-6 expression, hereditarily or as the result of therapies that cause impaired IL-6 expression (e.g., statin therapy) and/or subjects that also are being treated with PPARγ agonists (e.g., diabetics). Such subjects can be prone to delayed wound healing. Such delayed wound healing is commonly observed in diabetic ulcers.

Therefore, in another aspect, a method of promoting wound healing in a subject that has impaired IL-6 expression and/or a reduced STAT3 activation in myeloid cells (e.g., a subject undergoing statin and PPARγ agonist therapy). The method includes administering to the wound or about the periphery of the wound a therapeutically effective amount of IL-6 wherein a therapeutically effective amount is the amount of IL-6 to substantially decrease iNOS expression myeloid cells in a subject. In some aspects, the IL-6 can include recombinant IL-6 (rIL-6).

The wound treated by the method and/or compositions described herein can include any injury to any portion of the body of a subject (e.g., internal wound or external wound) including: acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries, such as cuts, incisions, excoriations, injuries sustained as result of accidents, ulcers, such as pressure ulcers, diabetic ulcers, plaster ulcers, and decubitus ulcer, post-surgical injuries. The wound can also include chronic conditions or wounds, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; tumor associated wounds. In one aspect of the invention, the wound can be related to sarcoidosis or cirrhosis in a subject.

A method of promoting wound healing in accordance with some aspects of the application can include restoring wound healing in a subject that has impaired IL-6 expression and/or a reduced STAT3 activation in myeloid cells where there has been a significant delay in wound healing. For example, it is often desirable to promote or increase the rate of healing in the case of both chronic wounds (such as diabetic, venous), acute (such as burns, penetrative injuries, or even wounds resulting from elective surgery), and for healing compromised individuals (such as immunodeficiencies and the elderly). In all examples, the wounds, and a delay in healing of the wounds, can in the worst-case lead to death, but in general severely decrease the quality of life. It will be appreciated that the present application is not limited to the preceding wounds or injuries and that other wounds or tissue injuries whether acute and/or chronic can be treated by the compositions and methods of the present invention.

In addition, an iNOS inhibitor can be administered alone or in combination with IL-6 for the promotion of wound healing in a subject. An iNOS inhibitor for use in the present invention can include the highly selective iNOS inhibitor, 1400 W (see Garvey et al. (1997) 1400*W is a Slow, Tight Binding, and Highly Selective Inhibitor of Inducible Nitric Oxide Synthase In vivo and In vitro.*, J Biol. Chem. February 21; 272(8):4959-63).

In other aspects, a TNF-α inhibitor can be administered to a subject alone or in combination with IL-6 in order to promote wound healing in a subject. A TNF-α inhibitor for use in the present invention can include a monoclonal antibody such as infliximab, adalimumab, certolizumab pegol, and golimumab, a circulating receptor fusion protein such as etanercept, or simple molecules such as xanthine derivatives (e.g., pentoxifylline) and bupropion.

Therefore, in another aspect a method of promoting wound healing in a subject that has impaired IL-6 expression and/or a reduced STAT3 activation in myeloid cells is provided. The method includes administering to the subject a therapeutically effective amount of IL-6, TNF-α inhibitor, and/or iNOS inhibitor to the subject wherein a therapeutically effective amount is the amount of IL-6, TNF-α inhibitor, and/or an iNOS inhibitor to substantially decrease iNOS expression in a subject.

In some aspects, the IL-6, TNF-α inhibitor, and/or iNOS inhibitor can be administered to a subject systemically. In some aspects, the anti IL-6, TNF-α inhibitor, and/or iNOS inhibitor can be administered directly to or about the periphery of a wound. In one example, the period of time that the IL-6, TNF-α inhibitor, and/or iNOS inhibitor is administered to the wound and/or proximate the wound can comprise from about onset of the wound and/or tissue injury to about days, weeks, or months after tissue injury.

The present application further relates to pharmaceutical compositions including IL-6, TNF-α inhibitor, and/or iNOS inhibitor described above. Examples of pharmaceutical compositions in accordance with the invention will generally include an amount of an IL-6, TNF-α inhibitor, and/or iNOS inhibitor admixed with an acceptable pharmaceutical diluent or excipient, such as a sterile aqueous solution, to give a range of final concentrations, depending on the intended use.

In another aspect of the invention, IL-6, TNF-α inhibitor, and/or iNOS inhibitor and pharmaceutical compositions thereof can be provided in and/or on a substrate, solid support, and/or wound dressing for delivery of the IL-6, TNF-α inhibitor, and/or iNOS inhibitor to the wound. As used herein, the term "substrate," or "solid support" and "wound dressing" refer broadly to any substrate when prepared for, and applied to, a wound for protection, absorbance, drainage, etc. The present invention may include any one of the numerous types of substrates and/or backings that are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer). The shape and size of a wound may be determined and the wound dressing customized for the exact site based on the measurements provided for the wound. As wound sites can vary in terms of mechanical strength, thickness, sensitivity, etc., the substrate can be molded to specifically address the mechanical and/or other needs of the site. For example, the thickness of the substrate may be minimized for locations that are highly innervated, e.g., the fingertips. Other wound sites, e.g., fingers, ankles, knees, elbows and the like, may be exposed to higher mechanical stress and require multiple layers of the substrate.

Pharmaceutical compositions described herein can also be provided in or on a surface of a medical device used to treat an internal and/or external wound. The medical device can comprise any instrument, implement, machine, contrivance, implant, or other similar or related article, including a component or part, or accessory, which is, for example, recognized in the official U.S. National Formulary, the U.S. Pharmacopoeia, or any supplement thereof; is intended for use in the diagnosis of disease or other conditions, or in the cure, mitigation, treatment, or prevention of disease, in humans or in other animals; or, is intended to affect the structure or any function of the body of humans or other animals, and which does not achieve any of its primary intended purposes through chemical action within or on the body of man or other animals, and which is not dependent upon being metabolized for the achievement of any of its primary intended purposes.

The following examples are included to demonstrate an embodiment of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

IL-6 and PPARγ Agonists Generate Hyper-Inflammatory Macrophages Leading to Tissue Destruction We found that treatment of myeloid cells (e.g., macrophages) with rosiglitazone in the absence of IL-6 in vitro and in vivo results in 1) synergistic hyper-inflammatory responses, 2) generation of pro-inflammatory, hyper-iNOS and TNF-γ expressing macrophages, and 3) drastic macrophage-mediated de novo tissue destruction. Our data demonstrate that hyperinflammatory macrophages are induced in several model systems suggesting that these findings may be clinically relevant to a large number of patients, given the common concurrence of relative states of IL-6 inhibition with PPARγ activation induced either by pharmacologic agonists or by endogenous ligands generated during inflammation and oxidant stress.

Methods
Mice

Pathogen-free, 6-8 week old female C57BL/6J wildtype mice were obtained from Jackson Laboratories (Bar Harbor, Me.). IL6$^{-/-}$ mice were originally obtained from Jackson Laboratories (Bar Harbor, Me.) and maintained for subsequent generations at the Animal Resource Center at CWRU (Cleveland, Ohio).

Immunofluorescence

Macrophages were defined as cells that stained positive for F4/80 and CD11b. For immunofluorescence staining of skin, 8 μm sections of frozen tissue was sectioned and fixed in 4° C. 100% acetone for 10 minutes. For i.p. and bone marrow derived macrophages, cells were washed with PBS and then fixed with 4% paraformaldehyde for 10 min at room temperature. After washing twice with PBS, cells were blocked in a solution of PBS containing 3% BSA, for 30 min at room temperature. For immunofluorescence of lung tissue, 5 μm sections were fixed in formalin, embedded in paraffin, and deparaffinized in xylene and ethanol. Primary and secondary antibodies were diluted as inidcated in 1×PBS. Primary and secondary antibodies were typically applied 90 minutes. Cells were washed three times with PBS between primary and secondary staining. The following antibodies were used for our analysis: anti-mouse F4/80 Antigen Alexa-488 BM8 (eBioscience, 1:100); Rat monoclonal [M1/70] to CD11b APC/Cy$_7$ (abcam, 1:20); rabbit anti-iNOS/iNOS II, NT (Millipore, 1:50). A secondary antibody conjugated to Alexa-405 was obtained from Invitrogen.

RT-PCR

For RT-PCR analysis, RNA was isolated using Trizol (Invitrogen) following the manufacturer's instructions, and was reverse-transcribed and quantified using Applied Biosystems TaqMan® RNA-to-CTT™ 1-Step Kit, TaqMan® Gene Expression Assays for 18s RNA, iNOS II, TNF-γ, and IL-1β, and Step-One™ System. Cycle time, temperature, and number were based on Applied Biosystems recommendations.

Wound Preparation, Treatment and Measurement

Skin was wounded with some modifications. Mice were treated with 3-6 mm excisional wounds, one midline and two on each side of the midline. At Day 0, wounds were measured lengthwise and widthwise, treated with 1 MED UVB, and treated topically with a 1% solution of rosiglitazone in 10 g Aquaphor. Wounds were measured and treated with topical rosiglitazone solution daily until healed (loss of serum crust and reepithelialization).

Lung Treatment and Preparation

Animals were anesthetized with avertin (250 mg/Kg, i.p., and taped to a surgical board). The neck area was thoroughly cleaned with betadine scrub and alcohol. A small midline skin incision (approx. 0.8 cm) was made in the neck and the trachea was exposed. Using a 27 gauge needle inserted between cartilaginous rings, 30 μl of phosphate-buffered saline containing 0.075 units of bleomycin was injected. The skin was closed with surgical glue (nexaband).

Alveolar Macrophages

Mice were injected intraperitoneally (i.p.) with a lethal dose of avertin (1 ml of 20 g/ml solution). Bronchoalveolar lavage (BAL) was performed by inserting a cannula through a cut in the trachea into the bronchi and infusing 3×0.5 ml aliquots of PBS. The BAL fluid sample was recovered by aspirating the liquid with a syringe; we recovered 80%±15% of instilled fluid volume. Macrophages were harvested following a spin down of the BAL fluid 25.

Peritoneal Macrophages

Mice were injected i.p. with 2 ml of thioglycollate and sacrificed 24 hours later mice by cervical dislocation. Lavage was performed by infusing 5 ml of 40C DPBS into the peritoneal cavity. The fluid sample is recovered by aspirating the liquid with a syringe. 80%±21% of instilled fluid volume is recovered. Macrophages were harvested following centrifugation of the BAL fluid.

Bone Marrow Derived Macrophages

Briefly, bone marrow cells were flushed aseptically from the dissected femurs of mice with PBS. The cells were cultured on 25 cm plates in DMEM containing 15% Fetal Calf Serum, 1% pen strep, 1% L-glutamine, 4.5 g/L glucose, and 20 μg/L MCSF. After 6 days, the media was changed to remove any cellular debris and non-adherent cells. The following day (day 7), the cells were carefully removed using lidocaine (4 mg/mL) and 10 mM EDTA in PBS at pH 7.5, and dispensed into 6 well plates at a concentration of 2×10$^6$ cells/well. Prior to experimentation, media was replaced with MCSF-free media containing 5 mM L-arginine.

Western Blot

NE-PER kit (Thermo Scientific) was used to extract nuclear and cytoplasmic protein from peritoneal macrophages. Protein samples were prepared under reduced conditions and western blot analysis was performed using a standard protocol (Invitrogen). Stat3 (79D7) Rabbit mAb, NF-κB p65, β-actin (13E5) Rabbit mAb (Cell Signaling Technology, Danvers, Mass.) were used for western blot evaluation. Densiometry analyzed by Biorad VersaDoc imaging system.

Antibodies and Reagents

Anti-TNF-α (abcam), rIL-6 (R&D Systems), anti-CD11b (AbD serotec) were all given i.p at a 1 μg/1 g body weight. 1400 W (Sigma) was given at a 10 μg/g dose. All other reagents were purchased from sigma.

Statistical Analysis

Data presented as means+s.e.m. P values were calculated using a two-tailed Student's t test for two samples of unequal variance. Statistical significance is indicated by an asterisk, and P values reported in figure legends.

Results

PPARγ Ligands Drive Hyper-Expression of iNOS and TNF-α in the Absence of IL-6

To investigate the effects of PPARγ activation in macrophages, we isolated primary bone marrow derived macrophages (BMDMs) from IL6$^{-/-}$ or matched wildtype C57BL/6 mice. As expected, in vitro stimulation of wildtype and IL6$^{-/-}$ BMDMs with LPS resulted in a modest upregulation of iNOS and TNF-α mRNA. However, pre-treatment of IL6$^{-/-}$ BMDMs with rosiglitazone followed by LPS stimulation produced striking increases in both iNOS and TNF-α expression (FIGS. 2A, B). To determine whether the in vitro response has in vivo significance, we utilized the model of thioglycollate-induced peritonitis to elicit a robust macrophage response in the peritoneum. Macrophages isolated from wildtype and IL6$^{-/-}$ mice subjected to peritoneal injury with or without in vivo rosiglitazone treatment were harvested and analyzed ex vivo. Similar to the in vitro results, rosiglitazone treated IL6$^{-/-}$ peritoneal macrophages expressed substantially higher levels of iNOS and TNF-α (FIGS. 3A, B). Confocal immunofluorescence microscopy using anti-CD11b and anti-F4/80 confirmed that the peritoneal cells were monocytes and macrophages (data not shown). To determine if generation of this hyper-inflammatory macrophage phenotype is driven by PPARγ and not an off-target effect of rosiglitazone, we utilized pioglitazone, another PPARγ agonist, and observed no significant difference between the two PPARγ agonists on iNOS or TNF-α expression (FIGS. 4A, B). To test if the pro-inflammatory effects were dependent on PPARγ signaling, IL6$^{-/-}$ mice were treated with either rosiglitazone or GW9662, a compound that binds the same receptor but does not signal through PPARγ. No significant increase in iNOS was observed in GW9662 treated mice demonstrating the importance of intact PPARγ signaling (FIG. 5). To determine if these in vivo findings were applicable in other organs, we utilized a lung injury model induced by bleomycin, a chemotherapeutic known to induce fibrosis and inflammation. Bronchoalveolar lavage (BAL) fluid was collected from mice 24 hours following treatment with either intratracheal bleomycin or sham intratracheal procedure with or without i.p. rosiglitazone treatment. As has been previously reported, macrophages are the predominant cell in BAL fluid (data not shown). Similar to the in vitro data and in vivo peritonitis data, bleomycin injury combined with IL-6 deficiency and systemic PPARγ agonist treatment induced significant expression of iNOS and TNF-γ expression in alveolar monocytes/macrophages (FIGS. 6A, B). These data demonstrate that organ injury combined with PPARγ activation and IL-6 deficiency leads to hyperinduction of iNOS and TNF-γ mRNA expression in infiltrating macrophages. Modest increases in iNOS and TNF-γ expression from mice treated with a sham procedure or bleomycin alone reflects inflammation due to tracheotomy-associated injury. To determine a potential mechanism for hyper-induction of iNOS under our treatment conditions, we examined transcription factors involved in the cooperative regulation of iNOS, specifically nuclear factor 03 (NF-κB), and signal transducer and activator of transcription 3 (STAT3). NF-κB is a potent activator of iNOS expression upregulated under inflammatory conditions. STAT3 has been previously demonstrated to inhibit NF-kB-mediated transactivation of iNOS, resulting in decreased iNOS expression. Additionally, PPARγ ligands have been shown to decrease STAT3 phosphorylation, a critical step for nuclear translocation of the transcription factor. Given this, we hypothesized that in our experimental condition, STAT3-mediated suppression of NF-κB transactivation of iNOS is diminished, resulting in hyper-induction of iNOS. Thioglycollate-elicited macrophages harvested from both IL6$^{-/-}$ and WT mice were treated with rosiglitazone ex vivo followed by LPS stimulation. Timepoint analysis of nuclear NF-κB p65 and STAT3 fold change from 30 to 60 minutes show a striking increase in NF-kB p65 with concomitant decrease of STAT3 in IL6–/– macrophages treated with rosiglitazone and LPS (FIGS. 7A, B). Interestingly, the combination of rosiglitazone and a stimulatory agent, in the absence of IL-6, is the treatment condition in which we observe hyper-induction of iNOS (FIGS. 2-7). Reconstitution of IL6–/– macrophages with recombinant IL-6 (rIL6) restores STAT3 and NF-kB levels similar to wildtype conditions (FIG. 7B).

Hyper Inflammatory Macrophage Generation In Situ

Next, we investigated the effects of PPARγ activity on macrophages in situ using models of pneumonitis and dermatitis. As was observed in BAL macrophages (FIGS. 8A,B), RTPCR of RNA from whole lungs revealed increased iNOS and TNF-α expression when treated with a PPARγ agonist in IL6$^{-/-}$ mice, starting at 6 hours (data not shown) and peaking at 24 hours (FIGS. 8A,B). No increases in iNOS or TNF-γ were observed in wildtype counterparts. To determine the cellular source of whole lung iNOS expression, lung sections were stained with antibodies against monocytes/macrophage markers F4/80 and CD11b, and iNOS. Although confocal microscopy demonstrated colocalization of CD11b and F4/80, little iNOS staining was observed in wildtype animals treated with bleomycin and rosiglitazone (FIG. 9A). IL6$^{-/-}$ mice treated in an identical manner displayed intense staining of iNOS which colocalized with CD11b$^+$F4/80$^+$ macrophages (FIG. 9B). Little iNOS staining was observed in either wildtype or IL6$^{-/-}$ mice treated with bleomycin or rosiglitazone alone (FIG. 18A-F). In the skin, IL6$^{-/-}$ and wildtype mice were subjected to excisional biopsies on dorsal skin followed by a single dose of 72 mJ/cm$^2$ UVB and topical application of rosiglitazone. This dose of UVB has been previously shown to recruit monocytes and macrophages into the skin. In wildtype mice, rosiglitazone or UVB alone, or in combination, did not result in a significant increase of iNOS and TNF-α expression. A similar modest induction of iNOS and TNF-α mRNA was observed in IL6$^{-/-}$ mice, except in the combined wounding, UVB, and rosiglitazone treatment condition. This combination resulted in a 20-fold and 13-fold increase in iNOS and TNF-α mRNA expression at 24 hours, respectively (FIGS. 10 A, B). To determine the cellular source of iNOS, skin sections were stained for F4/80, CD11b, and iNOS. Confocal microscopy demonstrated low iNOS levels in wildtype animals (FIG. 11A), yet robust iNOS staining colocalized with CD11b+F4/80– monocytes and CD11b$^+$F4/80$^+$ macrophages in IL6$^{-/-}$ mice that were wounded prior to treatment with UVB and rosiglitazone (FIG. 11B). Taken together, the in vitro and in vivo results demonstrate that the presence of a PPARγ agonist in the absence of IL-6 generates hyper-inflammatory macrophages in multiple systems.

Hyper Inflammatory Macrophage Generation Leads to Destruction of Tissue

After observing significant increases in macrophage-derived inflammatory mediators and cytokines in our wound model, we hypothesized that increased iNOS and TNF-α expression would result in tissue destruction. Skin isolated from IL6$^{-/-}$ mice following the combination of UVB/rosiglitazone/wound treatment ("the inflammatory wound model") displayed a dense infiltrate of mononuclear cells by 9 hours post wounding compared to controls as illustrated by H&E staining (FIGS. 12A,B). Confocal microscopy demonstrated the presence of CD11b$^+$ and F4/80$^+$ cells in both IL6$^{-/-}$ and wildtype mice (FIGS. 12C, D). Surrounding wound skin was harvested at the indicated time points and analyzed for iNOS and TNF-α expression. Wildtype mice displayed minimal increases in iNOS and TNF-α. In contrast, iNOS and TNF-α were substantially upregulated in IL6$^{-/-}$ mice as early as 9 hours which coincides with the entry of monocytes and macrophages into the skin (FIGS. 13A, B). To determine the cellular specificity of iNOS, other leukocytes such as neutrophils were also examined. Corresponding tissue sections were stained for the neutrophil marker GR1 (Ly6g) and iNOS. No colocalization of iNOS with neutrophils was observed (FIG. 14A).

To verify that monocytes/macrophages were responsible for the excess inflammation and tissue destruction, we used clodronate liposomes which are selectively toxic to phagocytic cells to deplete monocytes/macrophages in the surrounding wound tissue. IL6$^{-/-}$ mice were subjected to the inflammatory wound model followed by intradermal injections of either clodronate or PBS control liposomes in the surrounding wound areas. After 24 hours wounds from IL6$^{-/-}$ mice treated with PBS control liposomes exhibited dermal edema composed of a dense infiltrate of inflammatory cells in the dermis and subcutis. At 48 hours the skin exhibited epidermal necrosis and superficial dermal necrosis (FIG. 14B). In contrast, wounds from IL6$^{-/-}$ mice treated with clodronate liposomes resulted in normal appearing tissue with preservation of the epidermis and dermis, and a sparse mononuclear cell infiltrate in the dermis and subcutis (FIG. 14C). We thus conclude that in the absence of IL-6, PPARγ ligands drive macrophages towards a high iNOS and TNF-α hyper inflammatory state propagating inflammation and tissue destruction.

Hyper-Inflammatory Macrophage Generation Leads to a Delay in Wound Healing

Next we asked whether the increased macrophage-derived inflammatory factors would affect the duration of wound healing. IL6$^{-/-}$ and wildtype mice were subjected to the previously described inflammatory wound protocol. Wounds from each mouse were measured daily and wound healing curves were generated based on the percentage of the initial total wound area. Wounds in IL6$^{-/-}$ mice topically treated with rosiglitazone drastically expanded compared to wildtype animals with comparable initial wound size at day 0 (FIG. 15A). By day 3, wounds in IL6$^{-/-}$ mice show visible inflammation in the intact skin between the wound sites and little contraction compared to wildtype. By day 9, the wounds of wildtype mice had progressed towards resolution, while the wounds of IL6$^{-/-}$ mice remained enlarged above baseline (FIG. 15B). Strikingly, wound closure was delayed by 8 days in IL6$^{-/-}$ mice compared to wildtype. Mice given daily i.p injections of rosiglitazone also demonstrated wound expansion (data not shown), indicating that the route of drug administration was not critical for subsequent macrophage-mediated destruction. Wound closure was unaffected by treatment with rosiglitazone alone, UVB alone, or vehicle alone (FIG. 19A-D). To confirm the criticality of IL-6 in this model, we tested whether reconstitution with rIL-6 in IL6$^{-/-}$ animals would restore normal wound healing. Wounds of rIL-6 reconstituted mice demonstrate normal wound healing with resolution by day 11, similar to wildtype (FIG. 15b).

To further confirm the role of macrophages in mediating tissue destruction, we tested whether blocking macrophage entry into the skin using an antibody against CD11b would restore tissue morphology. Anti-CD11b treatment has been previously shown to prevent infiltration of monocytic cells elicited by UVB into the skin35. IL6$^{-/-}$ mice were subjected to the wound treatment along with either i.p. anti-CD11b. Skin wounds harvested at 24 hours in IL6$^{-/-}$ mice treated with isotype control exhibit epidermal necrosis, superficial dermal necrosis, dermal edema, and a dense infiltrate of inflammatory cells in the subcutis. In contrast, wounds of IL6$^{-/-}$ mice treated with i.p. injections of anti-CD11b had intact epidermis and dermis with a sparse mononuclear infiltrate in the subcutis (FIG. 15C). Confocal microscopy confirmed numerous CD11b$^+$ and F4/80$^+$ cells in skin harvested 24 hours after wounding from IL6$^{-/-}$ mice injected with isotype control in contrast to sparse staining in skin of mice treated with anti-CD11b (FIG. 15D). Expression levels of iNOS and TNF-α were substantially lower in the IL6$^{-/-}$ mice injected with anti-CD11b versus isotype control demonstrating the role of macrophages in expression of these inflammatory mediators (FIGS. 16 A, B). To further test the roles of macrophages in delayed wound healing, we generated a wound healing curve for IL6$^{-/-}$ mice subjected to inflammatory wound treatment and injected i.p. with anti-CD11b. Wounds from mice injected with anti-CD11b remained above baseline until day 5 and were fully healed by day 13. In contrast, wounds of mice injected with CD11b isotype control remained above baseline until day 7, and did not heal until day 21 (FIG. 17A). Lastly, to demonstrate the roles of iNOS and TNF-α in our inflammatory wound model, we generated wound healing curves for IL6$^{-/-}$ mice subjected to inflammatory wound treatment and a single i.p. injection with either 1400 W (a specific iNOS inhibitor) or a single injection of anti-TNF-α 1 hour prior to wounding. The wounds from animals treated with 1400 W display a normal healing pattern, healing by day 14, compared to day 23 for PBS-injected mice (FIG. 17B). Lastly, wounds from IL6$^{-/-}$ mice treated with anti-TNF-α antibody regain a normal healing pattern and heal by day 12, compared to day 23 for isotype control injected mice (FIG. 17C).

EXAMPLE 2

Figure 20:
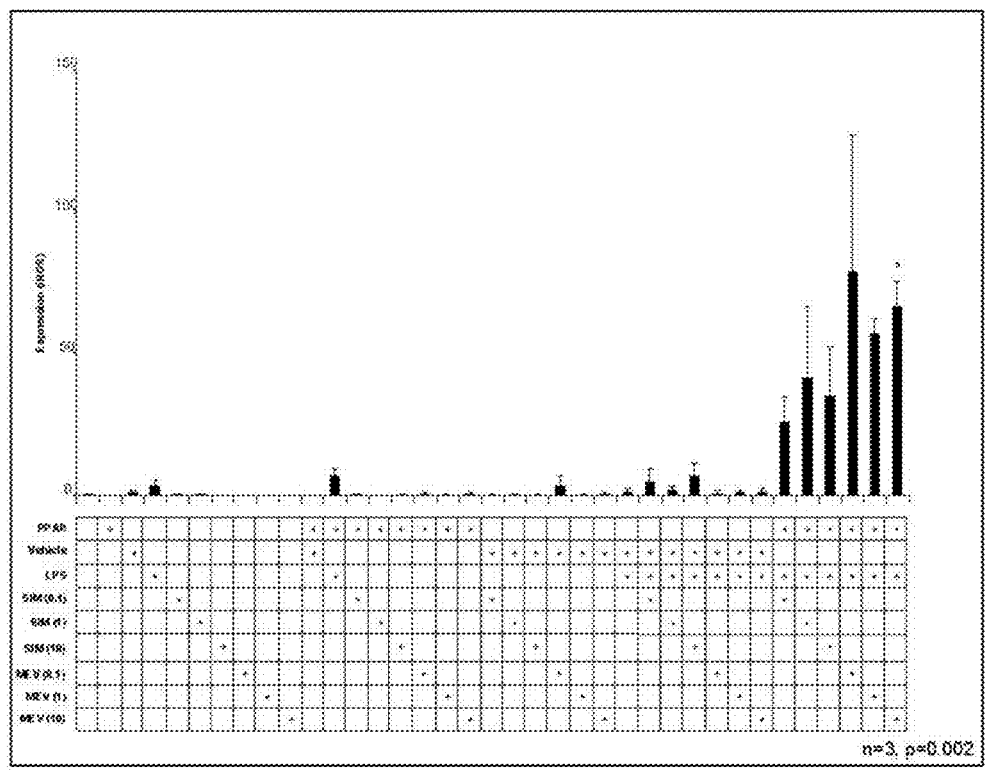
FIG. 20 illustrates a chart showing iNOS expression of ex vivo elicited peritoneal macrophages from WT (C57B1/6 mice) plated in 24 well plates, treated with Rosiglitazone (5 uM) and/or Simvistatin (Sim) or Mevistatin (Mev) at 0.1, 1, and 10 µM concentrations for 16 hours, and then stimulated with 1 ng/mL LPS for 4 hours.
Figure 21:
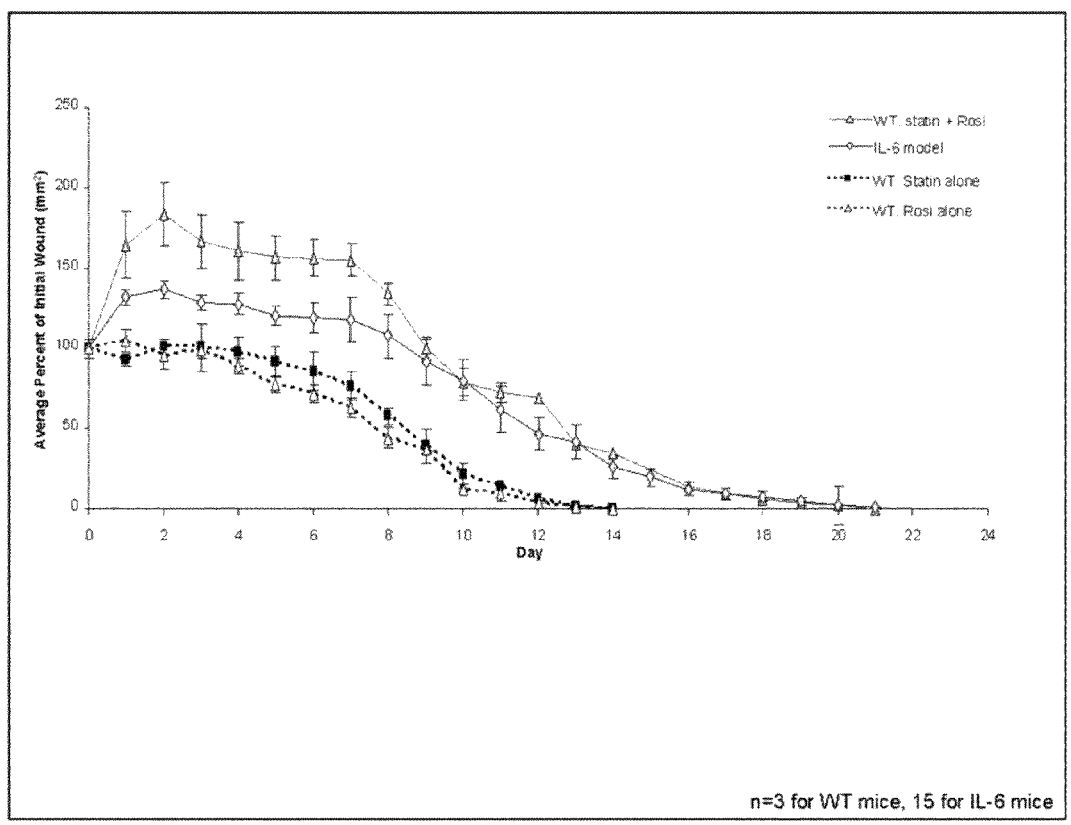
FIG. 21 illustrates a wound healing graph showing WT (c57BL/6) mice aged 6-8 weeks subjected to a cutaneous wounding protocol and injected with 0.6 mg of simvistatin 2 hours prior to wounding and treated topically with a 1% solution of rosiglitazone in 10 g Aquaphor. Wounds were measured and treated with topical rosiglitazone solution daily until healed (loss of serum crust and reepithelialization).

Combination of Statin and PPAR-γ Agonist Generates Paradoxical Hyper-Inflammation and Tissue Destruction We found that PPAR-γ agonist rosiglitazone, its presence in the absence of IL-6 paradoxically drives macrophages to express super-elevated levels of iNOS resulting in tissue destruction and delayed wound healing. We were interested in investigating the interaction of statins with rosiglitazone, because statins have been shown to reduce IL-6 and clinically, these medications are often co-prescribed in type II diabetics for cardiovascular disease prevention. We found that that LPS stimulation of macrophages pre-treated with mevastatin and rosiglitazone results in an 18.3-fold increase in iNOS expression compared to LPS alone (n=3, p=0.002) (FIG. 20). In vivo studies demonstrate that i.p. injection of simvastatin to mice prior to wounding, followed by daily topical rosiglitazone administration, results in tissue destruction and a nine day delay in wound healing (n=3) (FIG. 21). We found that the mechanism of increased iNOS following treatment is due to a decreased ability of STAT3 to transrepress NF-κB activity in the nucleus, resulting in unregulated iNOS expression. LPS stimulation of statin and rosiglitazone pretreated macrophages results in upregulation of SOCS3 in the cytoplasm followed by a decrease in STATS with a concomitant increase in NF-κB accumulation in the nucleus (n=2). In summary, we demonstrate that the presence of two medications with known anti-inflammatory properties, rosiglitazone and mevastatin, results in a paradoxical increase in inflammation and a tissue destructive phenotype.

EXAMPLE 3

Human HiNOS Generation with Combination of Statin and PPAR-γ Agonist

Figure 22:
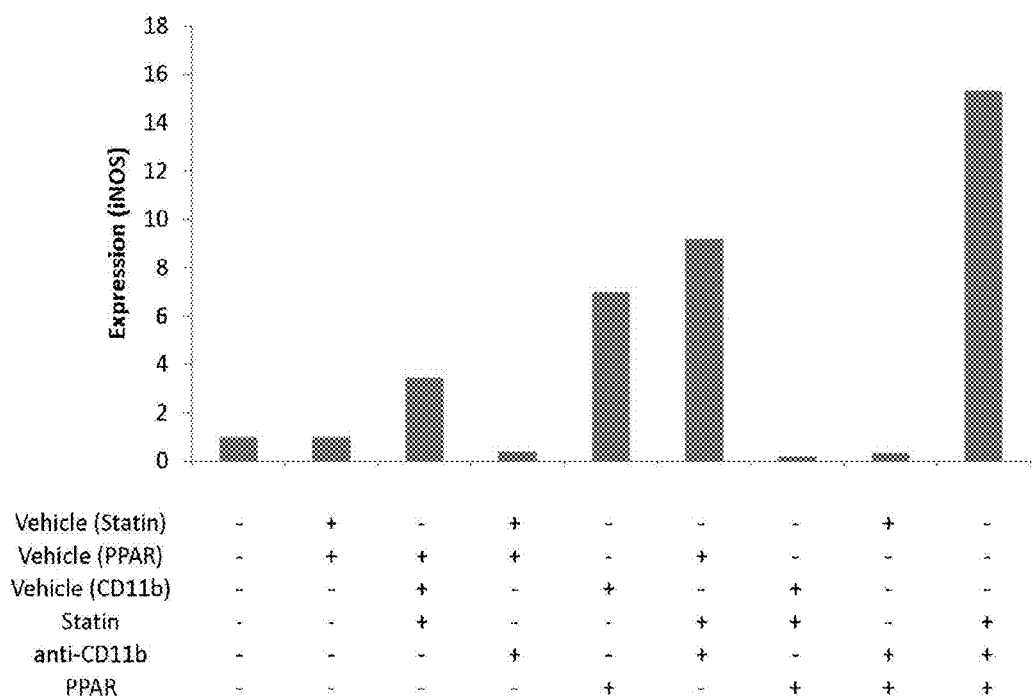
FIG. 22 illustrates a graph showing iNOS expression in human macrophages treated with statin, anti-CD11b, and PPAR.

FIG. 22 illustrates a graph showing iNOS expression in human macrophages treated with statin, anti-CD11b, and PPAR-γ agonist. We unexpectedly found that human macrophages treated with a statin and PPAR-γ agonist exhibit over express iNOS compared to controls and human macrophages treated with statin alone and PPAR-γ alone.
Monocyte Isolation Human monocytes were isolated by using plastic adherence technique. Briefly, heparinized whole blood was freshly drawn and was diluted 1:1 with phosphate-buffered saline (PBS). Blood/PBS was layered on Ficoll-Hypaque and was then centrifuged at 400 g. The mononuclear cell layer was collected and washed with PBS then resuspended with in bovine calf serum (BCS) in order to remove all the platelets. The mononuclear cells were then resuspended in 10% BCS/Dulbecco's Modified Eagle Medium (DMEM) to be plated on BCS-coated flask overnight to allow cells to adhere. After monocyte adherence, lymphocytes were removed by washing with DMEM. Monocytes were then collected with 5 mM EDTA and counted. Before using, monocytes were resuspended in 10% BCS/DMEM and is then ready to be used.
RT-PCR RNA was isolated using TRIzol reagent following to manufacturer's instructions. RT-PCR analysis was performed in a total volume of 25 uL. 200 nM of forward and reverse primers and 50 ng/uL cDNA was used. Primers used were the same as Mansouri et al.[3], which were: for iNOS, 5'-ACAT-TGATGAGAAGCTGTCCCAC-3' (sense) (SEQ ID NO: 1) and 5'-CAAAGGCTGTGAGTCCTGCAC-3' (anti-sense) (SEQ ID NO: 2); GAPDH, 5'-CAGAACATCATCCCTGC-CTCT-3' (sense) (SEQ ID NO: 3) and 5'-GCTTGA-CAAAGTGGTCGTTGAG-3' (anti-sense) (SEQ ID NO: 4).

EXAMPLE 4

We found that hyper-inflammatory macrophages exhibit remarkable cytotoxicity against B16 melanoma cells in vitro. Preliminary observations demonstrate decreased established/confluent B16 cells two days after the introduction of hyper-inflammatory macrophages.

Figure 23:
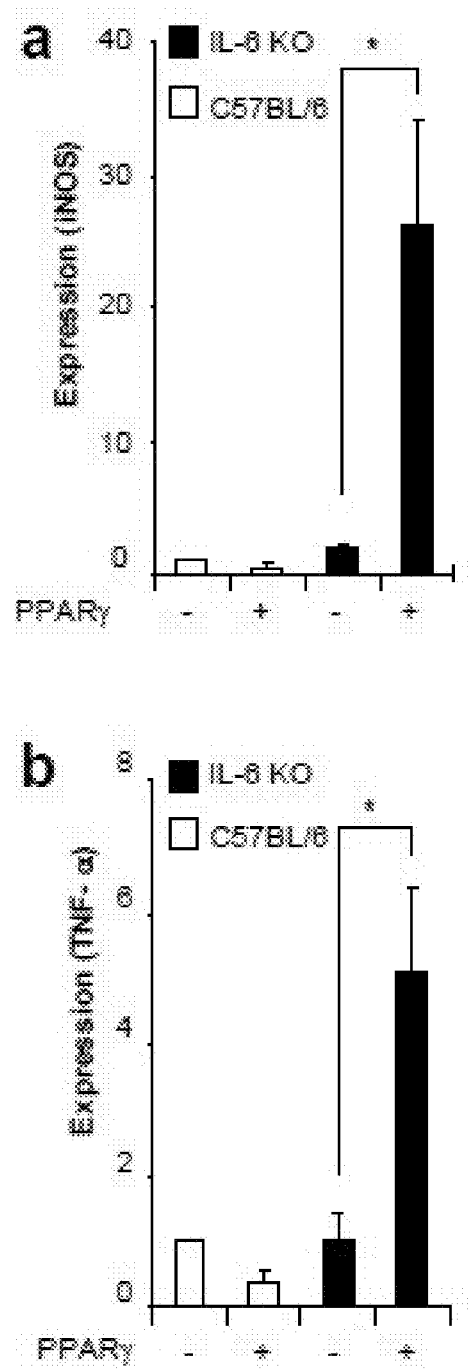
FIG. 23 illustrates graphs showing (A) iNOS expression and (B) TNF-α expression of peritoneal macrophages isolated from C57BL/6 and IL6−/− mice treated in vivo with a PPARγ agonist as indicated.

We postulated that these super-inflammatory macrophages possess the ability to overcome and exploit the known interactions between macrophages and melanoma and thus may be effective in the destruction of neoplastic cells. We tested this hypothesis by co-culturing B16 melanoma cells with thioglycollate-elicited intra-peritoneal macrophages from wild type C57BL/6 and IL-6 knockout mice. A 4:1 E:T ratio was used per well and the co-culture was carried out for forty-eight hours. In vivo elicited peritoneal macrophages were treated with a PPAR-γ agonist. FIG. 23 illustrates graphs showing (A) iNOS expression and (B) TNF-α expression of peritoneal macrophages isolated from C57BL/6 and IL6$^{-/-}$ mice treated in vivo with a PPARγ agonist as indicated. Most remarkable was the significant reduction in B16 cells despite being allowed to form a well-established mono-layer for twenty four hours (FIGS. 24B, C) prior to the addition of hyper-inflammatory macrophages. There was no noticeable reduction in the B16 melanoma cells when co-cultured with macrophages obtained from wild-type mice (FIGS. 24A, D).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:
1. A method of generating a hyper iNOS expressing cell comprising: administering to a myeloid derived cell an amount of a PPARγ agonist and an IL-6/STAT3 signaling pathway antagonist effective to substantially inhibit STAT3 activation in the cell and administering an inflammatory insult to the cell to stimulate hyper iNOS expression from the cell.

2. The method of claim 1, the myeloid derived cell comprising a macrophage or monocyte.

3. The method of claim 1, wherein the hyper iNOS expressing cell is generated in vitro.

4. The method of claim 1, wherein the hyper iNOS expressing cell is generated in vivo.

5. The method of claim 1, the PPARγ agonist comprising a thiazolidinedione or a derivative thereof.

6. The method of claim 1, the PPARγ agonist comprising at least one compound or a pharmaceutically salt thereof selected from the group consisting of: (+)-5[[4-[(3,4-dihydro-6-hydroxy-2,5,7,8-tetramethyl-2H-1-benzopyran-2-yl)methoxy]phenyl]methyl]-2,4-thiazolidinedione; 5-[4-[2-(5-ethylpyridin-2-yl)ethoxyl]benzyl]thiazolidine-2,4-dione; 5-[4-[(1-methylcyclohexyl)methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino]ethoxy]benzyl]-5-methlthiazolidine-2,4-dione; 5-[4-[2-[2,4-dioxo-5-phenylthiazolidine-3-yl]ethoxy]benzyl]thiazolidine-2,4-dione; 5-[4-[2-[(N-methyl-N-(phenoxycarbonyl)amino]ethoxy]benzyl]thiazolidine-2,4-dione; 5-[4-[2-phenoxyethoxy]benzyl]thiazolidine-2,4-dione; 5-[4-[2-(4-chorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl]thiazolidine-2,4-dione; 5-[(2-benzyl-2,3-dihydrobenzopyran)-5-ylmethyl]thiazolidine-2,4-dione; 5-[[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy]benzyl]thiazolidine-2,4-dione; 5-[4-[3-(5-methyl-2-phenyloxazol-4-yl)propionyl]benzyl]thiazolidine-2,4-dione; 5-[2-(5-methyl-2-phenyloxazol-4-ylmethyl)benzofuran-5-ylmethyl]oxazolidine-2,4-dione; 5-[4-[2-(N-methyl-N-(2-pyridyl)amino]ethoxy]benzyl]thiazolidine-2,4-dione; and 5-[4-[2-(N-(benzoxazol-2-yl)-N-methylamino]ethoxy]benzyl]oxazolidine-2,4-dione.

7. The method of claim 1, wherein the IL-6/STAT3 signaling pathway antagonist comprises at least one of an antibody, peptide, or small molecule.

8. The method of claim 7, wherein the IL-6/STAT3 signaling pathway antagonist is an HMG CoA reductase inhibitor.

9. The method of claim 7, wherein the IL-6/STAT3 signaling pathway antagonist is a STAT3 inhibitor.

10. A method of mediating local destruction of tissue in a subject comprising:

administering an amount of a PPARγ agonist and an IL-6/STAT3 signaling pathway antagonist to macrophages of the subject effective to substantially inhibit STAT3 activation in the macrophages; and administering an amount of an inflammatory or damaging insult to the tissue of the subject effective to induce hyper iNOS expression of the macrophages that are in or about the periphery of the tissue.

11. The method of claim 10, the insult being administered directly to or about the periphery of the tissue.

12. The method of claim 10, the insult comprising at least one of trauma, physical stress, chemical stress, biological stress, or radiation.

13. The method of claim 10, the PPARγ agonist comprising a thiazolidinedione or a derivative thereof.

14. The method of claim 10, the PPARγ agonist comprising at least one compound or a pharmaceutically salt thereof selected from the group consisting of: (+)-5[[4-[(3,4-dihydro-6-hydroxy-2,5,7,8-tetramethyl-2H-1-benzopyran-2-yl)methoxy]phenyl]methyl]-2,4-thiazolidinedione; 5-[4-[2-(5-ethylpyridin-2-yl)ethoxyl]benzyl]thiazolidine-2,4-dione; 5-[4-[(1-methylcyclohexyl)methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino]ethoxy]benzyl]-5-methlthiazolidine-2,4-dione; 5-[4-[2-[2,4-dioxo-5-phenylthiazolidine-3-yl]ethoxy]benzyl]thiazolidine-2,4-dione; 5-[4-[2-[(N-methyl-N-(phenoxycarbonyl)amino]ethoxy]benzyl]thiazolidine-2,4-dione; 5-[4-[2-phenoxyethoxy]benzyl]thiazolidine-2,4-dione; 5-[4-[2-(4-chorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl]thiazolidine-2,4-dione; 5-[(2-benzyl-2,3-dihydrobenzopyran)-5-ylmethyl]thiazolidine-2,4-dione; 5-[[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy]benzyl]thiazolidine-2,4-dione; 5-[4-[3-(5-methyl-2-phenyloxazol-4-yl)propionyl]benzyl]thiazolidine-2,4-dione; 5-[2-(5-methyl-2-phenyloxazol-4-ylmethyl)benzofuran-5-ylmethyl]oxazolidine-2,4-dione; 5-[4-[2-(N-methyl-N-(2-pyridyl)amino]ethoxy]benzyl]thiazolidine-2,4-dione; and 5-[4-[2-(N-(benzoxazol-2-yl)-N-methylamino]ethoxy]benzyl]oxazolidine-2,4-dione.

15. The method of claim 10, wherein the IL-6/STAT3 signaling pathway antagonist comprises at least one of an antibody, peptide, or small molecule.

16. The method of claim 15, wherein the IL-6/STAT3 signaling pathway antagonist is an HMG CoA reductase inhibitor.

17. The method of claim 15, wherein the IL-6/STAT3 signaling pathway antagonist is a STAT3 inhibitor.

18. The method of claim 10, the tissue comprising at least one of a scar, tattoo, hair follicle, actinic keratosis lesion, or neoplastic tissue.

19. The method of claim 18, the neoplastic tissue comprising cancer tissue.

* * * * *